US011253524B2

(12) United States Patent
Jin et al.

(10) Patent No.: US 11,253,524 B2
(45) Date of Patent: Feb. 22, 2022

(54) METABOLITES OF BICTEGRAVIR

(71) Applicant: Gilead Sciences, Inc., Foster City, CA (US)

(72) Inventors: Haolun Jin, Foster City, CA (US); Hyung-Jung Pyun, Fremont, CA (US); Bill J. Smith, San Mateo, CA (US); Raju Subramanian, San Mateo, CA (US); Jianhong Wang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/251,454

(22) Filed: Jan. 18, 2019

(65) Prior Publication Data

US 2019/0224206 A1 Jul. 25, 2019

Related U.S. Application Data

(60) Provisional application No. 62/619,478, filed on Jan. 19, 2018.

(51) Int. Cl.

| | | |
|---|---|---|
| *A61K 31/537* | (2006.01) | |
| *A61K 31/553* | (2006.01) | |
| *A61P 31/18* | (2006.01) | |
| *A61K 31/706* | (2006.01) | |
| *A61K 45/06* | (2006.01) | |
| *C07D 498/18* | (2006.01) | |
| *C07H 17/00* | (2006.01) | |
| *G01N 33/94* | (2006.01) | |

(52) U.S. Cl.
CPC .......... *A61K 31/537* (2013.01); *A61K 31/553* (2013.01); *A61K 31/706* (2013.01); *A61K 45/06* (2013.01); *A61P 31/18* (2018.01); *C07D 498/18* (2013.01); *C07H 17/00* (2013.01); *G01N 33/94* (2013.01)

(58) Field of Classification Search
CPC ... A61K 31/537; A61K 31/553; A61K 31/706
See application file for complete search history.

(56) References Cited

U.S. PATENT DOCUMENTS

| | | | | |
|---|---|---|---|---|
| 9,216,996 | B2 * | 12/2015 | Jin | ....................... A61K 31/498 |
| 9,663,528 | B2 | 5/2017 | Desai et al. | |
| 9,732,092 | B2 | 8/2017 | Jin et al. | |
| 10,035,809 | B2 | 7/2018 | Bacon et al. | |
| 2013/0165489 | A1 | 6/2013 | Cocklin et al. | |
| 2016/0176885 | A1 | 6/2016 | Jin et al. | |

FOREIGN PATENT DOCUMENTS

| | | |
|---|---|---|
| WO | WO 2005/113509 | 12/2005 |
| WO | WO 2009/062285 | 5/2009 |
| WO | WO 2010/130034 | 11/2010 |
| WO | WO 2012/003497 | 1/2012 |
| WO | WO 2012/003498 | 1/2012 |
| WO | WO 2012/145728 | 10/2012 |
| WO | WO 2013/006738 | 1/2013 |
| WO | WO 2013/006792 | 1/2013 |
| WO | WO 2013/159064 | 10/2013 |
| WO | WO 2014/100212 | 6/2014 |
| WO | WO 2014/100323 | 6/2014 |

OTHER PUBLICATIONS

Bell, T. et al. (2018) "Multi-Discipline Review" *Center for Drug Evaluation and Research*, 1-435.
Food and Drug Administration (2003) "Guidance for Industry Bioavailability and Bioequivalence Studies for Orally Administered Drug Products—General Considerations" *U.S. Department of Health and Human Services (CDER)* 1-23.
Gallant, J. et al. (2017) "Antiviral Activity, Safety, and Pharmacokinetics of Bictegravir as 10-Day Monotherapy in HIV-1", *J Acquir Immune Defic Syndr.* 75(1):61-66.
Gallant, J. et al. (2017) "Bictegravir, emtricitabine, and tenofovir alafenamide versus dolutegravir, abacavir, and lamivudine for initial treatment of HIV-1 infection (GS-US-380-1489): a double-blind, multicentre, phase 3, randomised controlled non-inferiority trial" *The Lancet* 390: 2063-2072.
Intl. Search Report—Written Opinion dated Apr. 8, 2019 for PCT/US2019/014311.
Lazerwith, S. et al. (2016) "Discovery of Bictegravir (GS-9883), a Novel, Unboosted, Once-Daily HIV-1 Integrase Strand Transfer Inhibitor (INSTI) with Improved Pharmacokinetics and In Vitro Resistance Profile" ASM Microbe Poster #414, 1-15.
Reese, M. et al. (2012) "In Vitro Investigations into the Roles of Drug Transporters and Metabolizing Enzymes in the Disposition and Drug Interactions of Dolutegravir, a HIV Integrase Inhibitor" *Drug Metabolism and Disposition* 41(2):353-61.
Tsiang, M. et al. (2016) "Antiviral Activity of Bictegravir (GS-9883), a Novel Potent HIV-1 Integrase Strand Transfer Inhibitor with an Improved Resistance Profile" ASM Microbe Poster #416, 1-12.
Zhang, H. et al. (2017) "Clinical Pharmacology of the HIV Integrase Strand Transfer Inhibitor Bictegravir" *Croi Conference*, 1-2.
Williams, "Drug Metabolism", Foye's Principles of Medicinal Chemistry, 2008, Chapter 10, pp. 253-326.
Bell et al., "Uni-Review—NDA 210251: Bictegravir/emtricitabine/tenofovir alafenamide (B/F/TAF) FDC—BIKTARVY®", Center for Drug Evaluation and Research, 2018, 435 pages.
Bowers et al., "Disposition and metabolism of cabotegravir: a comparison of biotransformation and excretion between different species and routes of administration in humans", Xenobiotica, Jul. 2015, 17 pages.

(Continued)

*Primary Examiner* — Pancham Bakshi
(74) *Attorney, Agent, or Firm* — Fish & Richardson P.C.

(57) ABSTRACT

The present invention provides metabolites of the antiviral drug bictegravir, including compositions and salts thereof, which are useful in the prevention and/or treatment of HIV as well as analytical methods related to the administration of bictegravir.

4 Claims, 14 Drawing Sheets

(56) References Cited

OTHER PUBLICATIONS

ClinicalTrials.gov [online], "Pharmacokinetics of Bictegravir in Adults with Normal and Impaired Renal Function", U.S. National Library of Medicine, Mar. 2015, retrieved on May 26, 2021, retrieved from URL <".https://clinicaltrials.gov/ct2/show/NCT02400307?term=NCT02400307&draw=2&rank=1">, 8 pages.
ClinicalTrials.gov [online], "Study to Evaluate Safety, Pharmacokinetics, and Antiviral Activity of Bictegravir (GS-9883) in Human Immunodeficiency Virus (HIV)-1 Infected Participants", U.S. National Library of Medicine, Oct. 2014, retrieved on Apr. 9, 2021, retrieved from URL <".https://clinicaltrials.gov/ct2/show/NCT02275065">, 9 pages.
Costellino et al., "Metabolism, Excretion, and Mass Balance of the HIV-1 Integrase Inhibitor Dolutegravir in Humans", Antimicrobial Agents and Chemotherapy, Aug. 2013, 57(8): 3536-3546.
Food and Drug Administration, Safety Testing of Drug Metabolites Guidance for Industry, Pharmacology/Toxicology, Nov. 2016, 14 pages.
Penner et al., "Radiolabeled Absorption, Distribution, Metabolism, and Excretion Studies in Drug Development: Why, When and How?", Chemical Research in Toxicology, 2012, 25:513-531.
Smith et al., "Randomized controlled trial in HIV Infection [CROI Abstract 1251]", In Special Issue: Abstracts From the 2017 Conference on Retroviruses and Oportunistic Infections, Topics in Antiviral Medicine, 2017, 25(suppl 1):983, 3 pages.
Zhang et al., "Clinical Pharmacology of the Unboosted HIV Integrase Strand Transfer Inhibitor (INSTI) Bictegravir (BIC)", BHIVA Poster, Apr. 2017, 12 pages.
Australian Office Action in AU Patent Application No. 2019209594, dated Sep. 22, 2020, 5 pages.
European Office Action in EP Application No. 19703916.7, dated Aug. 26, 2020, 3 pages.
Indian Office Action in IN Patent Application No. 202017035059, dated Nov. 27, 2020, 7 pages.
PCT International Preliminary Report on Patentability in International Application No. PCT/US2019/014311, dated Jul. 21, 2020, 10 pages.
Tsiang et al., "Antiviral Activity of Bictegravir (GS-9883), a Novel Potent HIV-1 Integrase Strand Transfer Inhibitor with an Improved Resistance Profile", Antimicrobial Agents and Chemotherapy, 2016, 60(12): 7086-7097.
Zhang et al., "Clinical Pharmacology of the HIV Integrase Strand Transfer Inhibitor Bictegravir," Sexually Transmitted Infections, 2017, 93(Suppl 1):A74, P176.
Japanese Office Action in JP Patent Application No. 2020-539242, dated Aug. 31, 2021, 5 pages (with English translation).
PCT Third Party Observation in International Application No. PCT/US2019/014311, dated May 19, 2020, 14 pages.
Canadian Office Action in CA Patent Application No. 3,087,359, dated Oct. 1, 2021, 5 pages.

* cited by examiner

METABOLITES OF BICTEGRAVIR

CROSS REFERENCE TO RELATED APPLICATIONS

This patent application claims the benefit of priority of U.S. Provisional Patent Application Ser. No. 62/619,478, filed Jan. 19, 2018. The contents of this application are incorporated herein by reference.

FIELD OF THE INVENTION

The present invention provides metabolites of the antiviral drug bictegravir, including compositions and salts thereof, which are useful in the prevention and/or treatment of HIV as well as analytical methods related to the administration of bictegravir.

BACKGROUND OF THE INVENTION

The HIV/AIDS pandemic has claimed the lives of millions of people, and millions more are currently infected. Antiretroviral therapy has turned HIV infection into a chronic, manageable disease; however, no cure yet exists for HIV. Patients must remain on therapy for their whole lives making drug resistance an ongoing issue. Additionally, as patients age, concomitant treatment for other diseases and conditions becomes more common, increasing the potential for drug-drug interactions with HIV antiviral treatment. Accordingly, continued development of new antiviral drugs and combination therapies are a priority in the field of HIV therapeutics.

Integrase strand transfer inhibitors (INSTIs) are a class of antiretroviral drugs that act by inhibiting the essential HIV protein integrase from inserting the viral DNA genome into the host cell's chromatin. An example INSTI is bictegravir (BIC) which is currently being tested in human clinical trials in combination with emtricitabine (FTC), and tenofovir alafenamide (TAF). Bictegravir has the molecular structure shown below and is described in WO 2014/100212.

(Compound I)

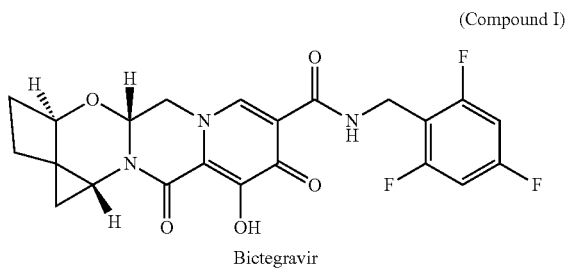 [SMILES: O=C(NCc1c(F)cc(F)cc1F)c1cn2c(c(O)c1=O)C(=O)N1[C@@H](C2)O[C@@H]2CCC23C[C@@H]13]

Bictegravir

In view of widespread HIV infection and the challenges in overcoming drug resistances and drug-drug interactions, there is a continuing need for new and improved antiviral agents. The metabolites of bictegravir, as well as their compositions and methods of use described herein, are directed toward fulfilling this need.

SUMMARY OF THE INVENTION

The present invention provides a compound selected from:

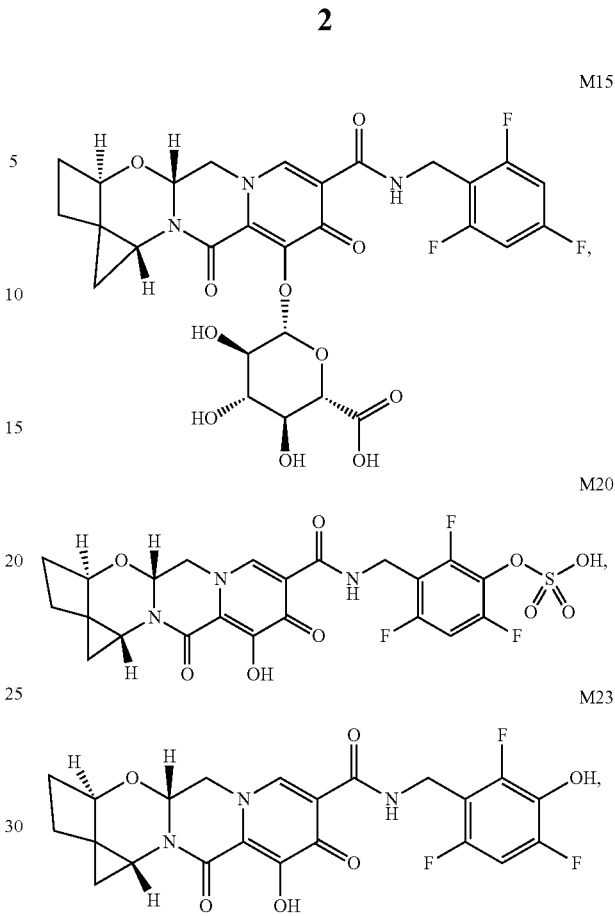

or a pharmaceutically acceptable salt thereof, which is substantially isolated.

The present invention further provides compositions comprising a compound of the invention, or pharmaceutically acceptable salt thereof, and at least one pharmaceutically acceptable carrier.

The present invention further provides preparations comprising a compound of the invention, or a pharmaceutically acceptable salt thereof.

The present invention further provides methods of preventing or treating an HIV infection in a human by administering to the human a therapeutically effective amount of a compound of the invention, or a pharmaceutically acceptable salt thereof.

The present invention further provides methods of detecting or confirming the administration of bictegravir to a patient, comprising identifying a compound of the invention, or a salt thereof, in a biological sample obtained from the patient.

The present invention further provides methods of measuring the rate of metabolism of bictegravir in a patient comprising measuring the amount of a compound of the invention, or a salt thereof, in the patient at one or more time points after administration of bictegravir.

The present invention further provides methods of determining the prophylactic or therapeutic response of a patient to bictegravir in the treatment of HIV infection, comprising measuring the amount of a compound of the invention, or a salt thereof, in the patient at one or more time points after administration of bictegravir.

The present invention further provides methods of optimizing the dose of bictegravir for a patient in need of treatment with bictegravir, comprising measuring the amount of a compound of the invention, or a salt thereof, in the patient at one or more time points after administration of bictegravir.

DETAILED DESCRIPTION

Figure 1:
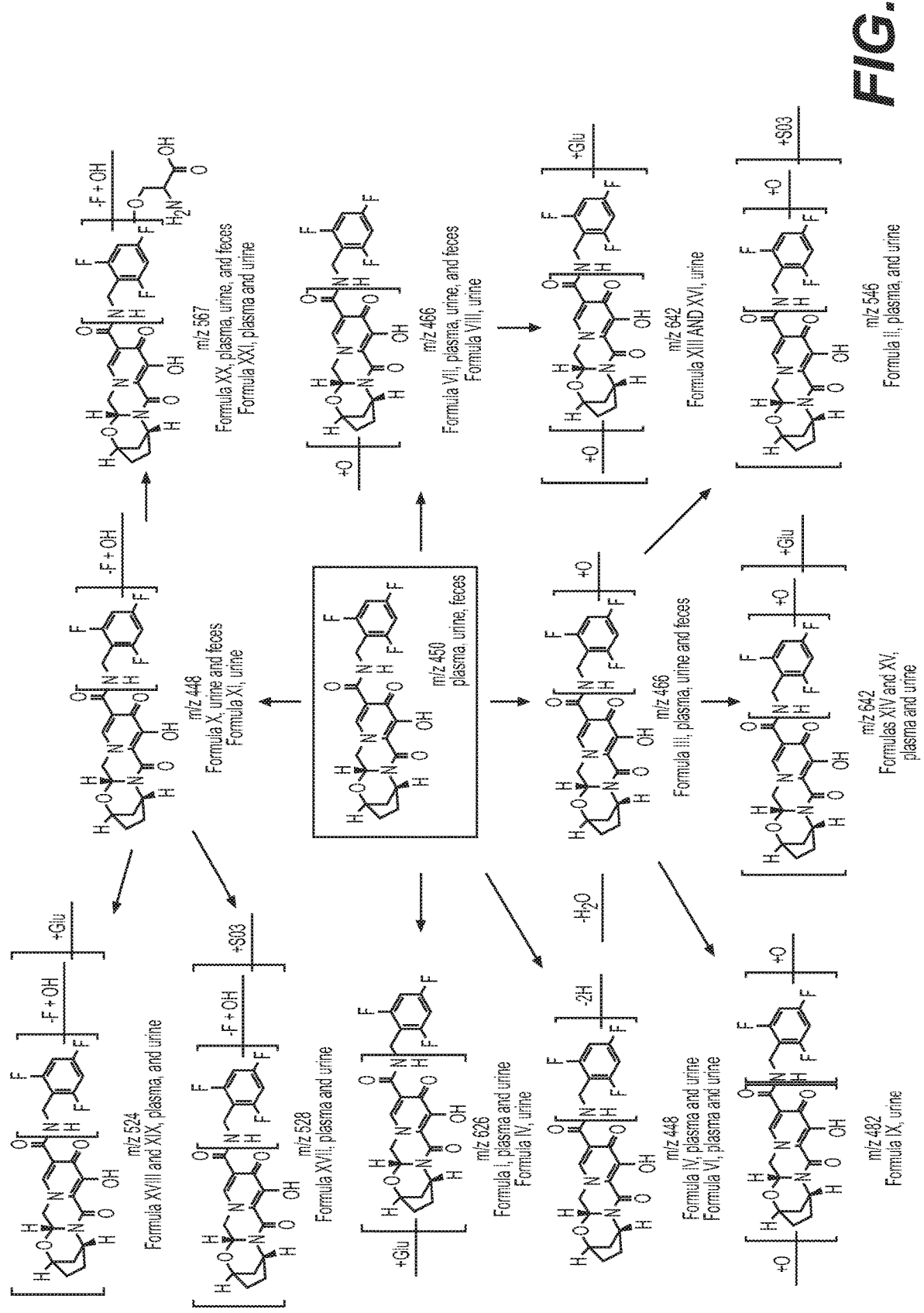
FIG. 1 shows the proposed structures of metabolites and biotransformation pathways of bictegravir in human plasma, urine, and feces following a single 100 μCi/100 mg oral dose of [$^{14}$C]bictegravir to healthy male adult human subjects.

The present invention is directed to metabolites of bictegravir and uses thereof. In some embodiments, the metabolite is bictegravir which has undergone (1) glucuronidation, (2) dehydrogenation, (3) hydroxylation, (4) hydroxylation with a loss of fluoride, (5) sulfation or glucuronic acid conjugation of the hydroxy-bictegravir, (6) sulfation or glucuronic acid or cysteine conjugation of desfluoro-hydroxy-bictegravir, or (7) a combination thereof. In some embodiments, the metabolite is selected from M15, M58, M51, M52, M21, M23, M54, M55, M22, M53, M20, M35, M12, M59, M45, M56, M16, M57, M9, and M37 (See FIG. 1). In some embodiments, the metabolite is selected from M465a, M465b, M465c, M305, M625, M641, and M611 (see FIG. 12).

In some embodiments, the metabolite is a compound selected from M15, M20, and M23:

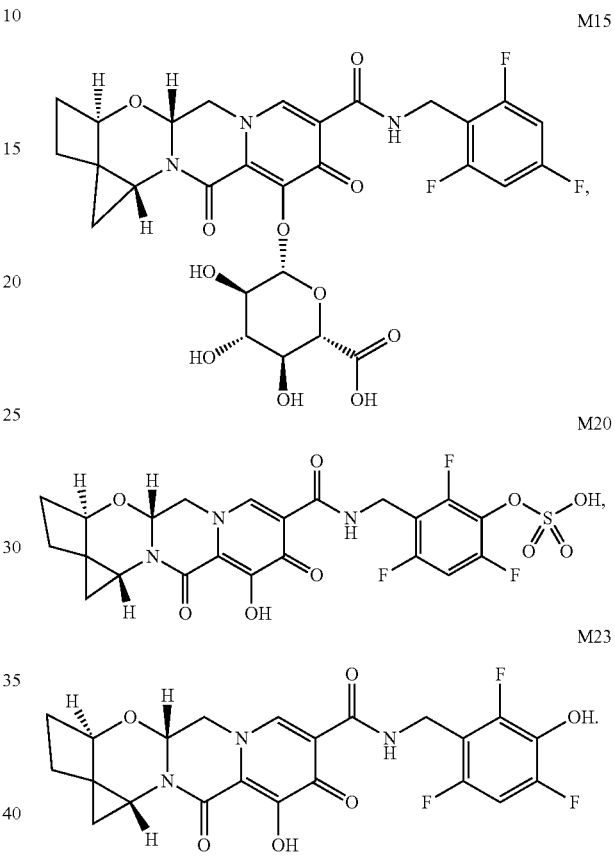

In some embodiments, the metabolite is a compound selected from M15 and M20. In some embodiments, the metabolite is M15. In some embodiments, the metabolite is M20. In some embodiments, the metabolite is M23.

The present invention further includes salts of the metabolites of the invention, such as pharmaceutically acceptable salts. A salt generally refers to a derivative of a disclosed compound wherein the parent compound is modified by converting an existing acid or base moiety to its salt form. A pharmaceutically acceptable salt is one that, within the scope of sound medical judgment, is suitable for use in contact with the tissues of human beings and animals without excessive toxicity, irritation, allergic response, or other problem or complication, commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. In one particular embodiment, the pharmaceutically acceptable salt is a sodium salt.

In some embodiments, the metabolite compounds, or salts thereof, are substantially isolated. By "substantially isolated" is meant that the metabolite compound, or salt thereof, is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the metabolite, or salt thereof. In some embodiments, M15, M20, and M23 are substantially isolated.

A metabolite of the invention, or its salt, can be present in a composition where the composition includes at least one compound other than the metabolite. In some embodiments, the composition includes more than one metabolite of the invention. In some embodiments, the composition comprises one or more metabolites of the invention, or salts thereof, and bictegravir, or a salt thereof. Compositions can be mixtures containing a metabolite of the invention, or salt thereof, and one or more solvents, substrates, carriers, etc. In some embodiments, the composition comprises a metabolite of the invention, or salt thereof, in an amount greater than about 25% by weight. In some embodiments, the composition comprises a metabolite of the invention, or salt thereof, in an amount greater than about 50% by weight. In some embodiments, the composition comprises a metabolite of the invention, or salt thereof, in an amount greater than about 75% by weight. In some embodiments, the composition comprises a metabolite of the invention, or salt thereof, in an amount greater than about 80% by weight. In some embodiments, the composition comprises a metabolite of the invention, or salt thereof, in an amount greater than about 85% by weight. In some embodiments, the composition comprises a metabolite of the invention, or salt thereof, in an amount greater than about 90% by weight. In some embodiments, the composition comprises a metabolite of the invention, or salt thereof, in an amount greater than about 95% by weight.

A preparation of a metabolite of the invention, or salt thereof, can be prepared by chemical synthesis or by isolation of the metabolite from a biological sample. Preparations can have a purity of greater than about 50%, greater than about 60%, greater than about 70%, greater than about 80%, greater than about 90%, or greater than about 95% purity. Purity can be measured by any of conventional means, such as by chromatographic methods or spectroscopic methods like NMR, MS, LC-MS, etc.

The metabolites of the invention are asymmetric (e.g., having one or more stereocenters). All stereoisomers, such as enantiomers and diastereomers, are intended unless otherwise indicated. Methods on how to prepare optically active forms from optically active starting materials are known in the art, such as by resolution of racemic mixtures or by stereoselective synthesis.

Metabolites of the invention also include all isotopes of atoms occurring in the metabolites. Isotopes include those atoms having the same atomic number but different mass numbers. For example, isotopes of hydrogen include tritium and deuterium. In some embodiments, the metabolite includes at least one deuterium.

The term, "compound" or "metabolite," as used herein is meant to include all stereoisomers, geometric iosomers, tautomers, and isotopes of the structures depicted.

The term, "metabolite" as used herein is meant to include any and all metabolic derivatives of bictegravir, including derivatives that have undergone one or more transformative processes selected from (1) glucuronidation, (2) dehydrogenation, (3) hydroxylation, (4) hydroxylation with a loss of fluoride, (5) sulfation or glucuronic acid conjugation of the hydroxy-bictegravir, and (6) sulfation or glucuronic acid or cysteine conjugation of desfluoro-hydroxy-bictegravir. In some embodiments, the metabolites of the invention have undergone more than one transformative process, including metabolic transformation of a derivative of bictegravir that has already undergone one or more metabolic transformations.

The compound bictegravir can also be considered a prodrug of the metabolites of the invention (e.g., a prodrug of metabolites M15, M20, M23, and the like) because bictegravir metabolically transforms upon administration to provide the metabolites of the invention. Accordingly, bictegravir can be administered to a human as a means of providing a metabolite of the invention to the human, for example, for preventing or treating an HIV infection in the human.

The present invention further includes a pharmaceutical composition comprising a metabolite of the invention, or pharmaceutically acceptable salt thereof, and at least one pharmaceutically acceptable carrier. As used herein, "pharmaceutically acceptable carrier" is meant to refer to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Methods

The present invention further relates to a method of preventing or treating an HIV infection (e.g., HIV-1 and/or HIV-2) in a human by administering to the human a therapeutically effective amount of a metabolite of the invention, or a pharmaceutically acceptable salt thereof. The human may have or be at risk of having the infection.

The term "treatment" or "treating" as used herein is intended to mean the administration of a metabolite, composition thereof, or preparation thereof, according to the present invention to alleviate or eliminate symptoms of HIV infection and/or to reduce viral load in a patient. The term "prevention" or "preventing" refers to the administration of a metabolite, composition thereof, or preparation thereof, according to the present invention post-exposure of the human to the virus but before the appearance of symptoms of the disease, and/or prior to the detection of the virus in the blood. The terms also refer to prevention of the appearance of symptoms of the disease and/or to prevent the virus from reaching detectible levels in the blood. The term includes both pre-exposure prophylaxis, as well as post-exposure prophylaxis. The term also refers to prevention of perinatal transmission of HIV from mother to baby, by administration to the mother before giving birth and to the child within the first days of life.

The terms "effective amount" or "therapeutically effective amount" refer to an amount of a metabolite according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a metabolite according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Administration of the metabolites of the invention, or their pharmaceutically acceptable salts, can be carried out via any of the accepted modes of administration of agents for serving similar utilities. The pharmaceutical compositions of the invention can be prepared by combining a metabolite of the invention, or a pharmaceutically acceptable salt thereof, with an appropriate pharmaceutically acceptable carrier and, in specific embodiments, are formulated into preparations in solid, semi solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral, sublingual, buccal, rectal, vaginal, and intranasal. In a particular embodiment, pharmaceutical compositions of the invention are tablets. In another embodiment, pharmaceutical compositions of the invention are injection (intramuscular (IM) or intraperitoneal (IP)). Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings described herein.

The present invention further relates to a method of detecting or confirming the administration of bictegravir to a patient comprising identifying a metabolite of the invention, or salt thereof, in a biological sample obtained from the patient. In some embodiments, the biological sample is derived from plasma, urine, or feces.

The present invention further relates to a method of measuring the rate of metabolism of bictegravir in a patient comprising measuring the amount of metabolite, or salt thereof, in the patient at one or more time points after administration of bictegravir.

The present invention further relates to a method of determining the prophylactic or therapeutic response of a patient to bictegravir in the treatment of HIV infection comprising measuring the amount of a metabolite of the invention, or salt thereof, in the patient at one or more time points after administration of bictegravir.

The present invention further relates to a method of optimizing the dose of bictegravir for a patient in need of treatment with bictegravir comprising measuring the amount of a metabolite of the invention, or salt thereof, in the patient at one or more time points after administration of bictegravir. The amount of metabolite may be indicative of the rate at which the patient metabolizes bictegravir. Patients who metabolize bictegravir more quickly or more effectively than other patients may form higher amounts of metabolite and potentially require higher doses of bictegravir, or additional doses, compared with patients who metabolize bictegravir more slowly. Patients who metabolize bictegravir less quickly or less effectively than other patients may form lower amounts of metabolite and potentially require lower doses of bictegravir, or fewer doses, compared with patients who metabolize bictegravir more quickly. Accordingly, the method of optimizing the dose of bictegravir may further include determining whether the measured amounts of metabolite are higher or lower than average, and adjusting the dosage of bictegravir accordingly.

Measuring the amount of metabolite, or salt thereof, in a patient can be carried out by obtaining a biological sample from the patient and measuring the amount of metabolite, or salt thereof, in the sample. In some embodiments, the sample is blood. In other embodiments, the sample is plasma. In other embodiments, the sample is urine. In other embodiments, the sample is feces.

The term "patient" is meant to refer to a human or other mammals such as laboratory animals and household pets (e.g., cats, dogs, swine, cattle, sheep, goats, horses, rabbits), and non-domestic animals such as non-human primates, mammalian wildlife, and the like, that are in need of therapeutic or preventative treatment for a viral infection, such as HIV infection.

Combination Therapies

One or more additional pharmaceutical agents can be used in combination with the compounds, salts, and compositions of the present invention for preventing or treating an HIV infection (e.g., in a human patient). In some embodiments, the composition of the invention further comprises one or more additional therapeutic agents. In some embodiments, the composition of the invention further comprises one to three additional therapeutic agents (e.g., one to three anti-HIV agents). In some embodiments, the one or more one additional therapeutic agents is an anti-HIV agent.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof. In some embodiments, the anti-HIV agent is an HIV protease inhibitor, an HIV non-nucleoside inhibitor of reverse transcriptase, an HIV nucleoside inhibitor of reverse transcriptase, an HIV nucleotide inhibitors of reverse transcriptase, a pharmacokinetic enhancer, or combination thereof. In some embodiments, the anti-HIV agent is an HIV nucleoside inhibitor of reverse transcriptase, an HIV nucleotide inhibitors of reverse, or combination thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of raltegravir, elvitegravir, dolutegravir, cabotegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, BMS-538158, GSK364735C, BMS-707035, MK-2048, BA 011, and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of ritonavir, cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), and combinations thereof.

In certain embodiments, a metabolite disclosed herein, or a pharmaceutically acceptable salt thereof, is combined with two, three, four or more additional therapeutic agents. The two, three four or more additional therapeutic agents can be different therapeutic agents selected from the same class of therapeutic agents, or they can be selected from different classes of therapeutic agents. In a specific embodiment, a metabolite disclosed herein, or a pharmaceutically acceptable salt thereof, is combined with an HIV nucleotide or nucleoside inhibitor of reverse transcriptase and an HIV non-nucleoside inhibitor of reverse transcriptase. In another specific embodiment, a metabolite disclosed herein, or a pharmaceutically acceptable salt thereof, is combined with an HIV nucleotide or nucleoside inhibitor of reverse transcriptase, and an HIV protease inhibiting compound. In a further embodiment, a metabolite disclosed herein, or a pharmaceutically acceptable salt thereof, is combined with an HIV nucleotide or nucleoside inhibitor of reverse transcriptase, an HIV non-nucleoside inhibitor of reverse transcriptase, and an HIV protease inhibiting compound. In an additional embodiment, a metabolite disclosed herein, or a pharmaceutically acceptable salt thereof, is combined with an HIV nucleotide or nucleoside inhibitor of reverse transcriptase, an HIV non-nucleoside inhibitor of reverse transcriptase, and a pharmacokinetic enhancer.

In certain embodiments, when a metabolite disclosed herein is combined with one or more additional therapeutic agents as described above, the components of the composition are administered as a simultaneous or sequential regimen. When administered sequentially, the combination may be administered in two or more administrations.

In certain embodiments, a metabolite disclosed herein is combined with one or more additional therapeutic agents in a unitary dosage form for simultaneous administration to a patient, for example as a solid dosage form for oral administration (e.g., a fixed dose combination tablet).

In certain embodiments, a metabolite disclosed herein is administered with one or more additional therapeutic agents. Co-administration of a metabolite disclosed herein, or a pharmaceutically acceptable salt thereof, with one or more additional therapeutic agents generally refers to simultaneous or sequential administration of a compound disclosed herein and one or more additional therapeutic agents, such that therapeutically effective amounts of the metabolite and one or more additional therapeutic agents are both present in the body of the patient.

Co-administration includes administration of unit dosages of the metabolites disclosed herein before or after administration of unit dosages of one or more additional therapeutic agents, for example, administration of the metabolites disclosed herein within seconds, minutes, or hours of the administration of one or more additional therapeutic agents. For example, in some embodiments, a unit dose of a metabolite disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a metabolite disclosed herein within seconds or minutes. In some embodiments, a unit dose of a metabolite disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a metabolite disclosed herein.

Pharmaceutical Formulations and Dosage Forms

The pharmaceutical compositions disclosed herein can be prepared by methodologies well known in the pharmaceutical art. For example, in certain embodiments, a pharmaceutical composition intended to be administered by injection can prepared by combining a metabolite of the invention with sterile, distilled water so as to form a solution. In some embodiments, a surfactant is added to facilitate the formation of a homogeneous solution or suspension. Surfactants are compounds that non-covalently interact with the compound of the invention so as to facilitate dissolution or homogeneous suspension of the compound in the aqueous delivery system.

The metabolites of the invention, or their pharmaceutically acceptable salts, can be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Results of a Phase 1 Study to Evaluate the Pharmacokinetics, Metabolism, and Excretion of Bictegravir in Healthy Subjects Study Design The objectives of this study were: (1) to determine the mass balance of bictegravir following administration of a single, oral dose of radiolabeled carbon-14 ([$^{14}$C])bictegravir; (2) to evaluate the pharmacokinetics (PK) of bictegravir and its metabolite(s), where possible; (3) to determine the metabolite profile of bictegravir in humans following administration of a single, oral dose of radiolabeled [$^{14}$C]bictegravir; and (4) to assess the safety and tolerability of bictegravir.

This was a Phase 1, open-label, single center, mass-balance study to evaluate the PK, metabolism, and excretion of bictegravir following administration of a single, oral dose of radiolabeled [$^{14}$C]bictegravir in healthy subjects. A total of eight patents were enrolled. Subjects were healthy male nonsmokers, 18 to 45 years of age, inclusive, with a body mass index (BMI) from 19 to 30 kg/m2, inclusive, normal 12-lead electrocardiogram (ECG), normal renal function, no significant medical history, and in good general health, as determined by the investigator at the screening evaluation performed no more than 28 days prior to the scheduled first dose.

Treatment involved a single, oral dose followed by a 6- to 21-day sample collection period, the exact duration of which was based on recovery of radiolabeled drug. The dose was 100 mg bictegravir (99 mg of nonradiolabeled bictegravir [as the sodium salt form] plus approximately 100 ρCi [1 mg] radiolabeled [$^{14}$C]bictegravir) administered orally as an approximately 40-mL ethanolic solution (4:6 [v/v] water:ethanol, pH adjusted with HCl). Following administration, the dosing container was rinsed twice, each rinse with approximately 50 mL of cranberry juice, and administered to the subject. The entire study drug solution and cranberry juice rinse (total of approximately 140 mL) was taken within a 10 minute window.

Individual data and summary statistics for the percentage and cumulative percentage of total [$^{14}$C]-radioactive dose recovered in urine, stool, and both samples were provided per sampling time. Individual, mean (standard deviation [SD]), and median (first quartile [Q1], third quartile [Q3]) cumulative percentage of total [$^{14}$C]-radioactive dose recovered versus time profiles in urine, stool, and both samples were presented in time linear and Semi-Log Scales.

Individual subject concentration data and summary statistics of plasma, whole blood, urine, and stool samples per sampling time were presented for total [$^{14}$C]-radioactivity. The whole blood-to-plasma ratio of total [$^{14}$C]-radioactivity concentration was determined for each subject and tabulated with descriptive statistics. In addition, individual subject concentration data and summary statistics of plasma and urine samples per sampling time were presented for bictegravir.

[$^{14}$C]Bictegravir Metabolite Profiling in Plasma, Urine, and Feces

A total of 20 metabolites of bictegravir were identified in the metabolite profiling results by high performance liquid chromatography (HPLC)-MS/TopCount method. These metabolites were generated through several biotransformation pathways, including direct glucuronidation (M15 and M58), dehydrogenation (M51 and M52), hydroxylation (M21, M23, M54, and M55), hydroxylation with a loss of fluoride (M22 and M53), sulfation or glucuronic acid conjugation of the hydroxy-bictegravir (M20, M35, M12, M59, and M45), sulfation or glucuronic acid or cysteine conjugation of desfluoro-hydroxy-bictegravir (M56, M16, M57, M9, and M37) (FIG. 1).

Plasma: Metabolite profiling and quantitation in plasma was performed with samples pooled for individual subjects between 0 to 144 hours postdose. Bictegravir and 13 metabolites were identified in human plasma. [$^{14}$C]Bictegravir was the major circulatory radioactive component and M20 (hydroxy-bictegravir-sulfate) and M15 (bictegravir-glucuronide) were the major metabolites in plasma, accounting for 67.9%, 20.1%, and 8.6%, respectively, of the plasma AUC0-72 h (area under the concentration time curve) of total radioactivity. The AUC0-72 h ratios of minor metabolites M21 (hydroxy-bictegravir), M52 (dehydrogenation product), and M23/M51 (hydroxy-bictegravir/dehydrogenation product) relative to that of the total radioactivity were 2.0%, 0.6%, and 0.2%, respectively. All of the metabolites were BLQ (below limit of quantification) by 144 hours after dosing, indicating no long-lived metabolites.

Urine: Metabolite profiling and quantitation in urine was performed with samples pooled for individual subjects within the period of 0 to 96 hours postdose. Bictegravir and 20 metabolites were identified in human urine. M15 (co-eluted with M58, both bictegravir-glucuronides), was the major radioactive component in the urine, accounting for 21.4% of the administered dose. Minor or trace level metabolites (see FIG. 1) were below 2.2% of the dose. Recovered unchanged bictegravir was low in urine (3.6% of the dose), consistent with the LC/MS/MS results of bictegravir.

Feces: Metabolite profiling and quantitation in feces was performed with the feces samples pooled for individual subjects. The unchanged parent, M9 (desfluoro-hydroxy-bictegravir-cysteine conjugate), M21/M22 (hydroxy-bictegravir/desfluoro-hydroxy-bictegravir co-eluted), and M23 (hydroxy-bictegravir) accounted on average for 30.6%, 13.0%, 8.1%, and 3.6%, respectively, of the administered dose (quantitation averaged from 8 subjects within 0 to 144 hours postdose).

Identification of metabolites: Metabolites were identified by LC-MS/TopCount method. First, product ion mass spectra of the authentic bictegravir and [$^{14}$C]bictegravir reference standards were acquired on an LTQ ion trap mass spectrometer and an LTQ Orbitrap high resolution mass spectrometer. Then their major fragmentation patterns were proposed and the elemental compositions of the corresponding fragment ions were confirmed. Second, the retention times of the metabolites observed on LC-Radio-chromatograms were compared to the corresponding retention times on LC-MS chromatogram operating in a full scan positive ionization mode and the molecular ions of the metabolites were determined. Product ion mass spectra were then acquired for the molecular ions of the potential metabolites. Accurate mass spectra were also acquired on an LTQ Orbitrap high resolution mass spectrometer to confirm the chemical formulas of the proposed molecular ions and their product ions. The plausible fragmentation pathways and the putative metabolite structures were proposed (FIG. 1).

Metabolite M15 and M58 eluted at 25.74 and 25.44 min on LC-MS chromatogram and had molecular ions at m/z 626. Accurate mass measurement of these ions provided a chemical formula of $C_{27}H_{27}F_3N_3O_{11}^+$ with mass errors from 0.02 to 0.2 ppm suggesting an addition of $C_6H_8O_6$ moiety to the parent molecular ion. CID of these molecular ions resulted in similar fragmentation and showed major ions at m/z 450, corresponding to a neutral loss of −176 Da from the molecular ions. MS3 of the ion at m/z 450 showed spectra that matched the reference standard of bictegravir, indicating that M15 and M58 were the glucuronides of bictegravir.

Metabolites M54, M21, and M23 eluted at 31.40, 33.18, and 33.97 min, respectively, on the LC-MS chromatogram and all had molecular ions at m/z 466. Accurate mass measurement of these ions provided a chemical formula of $C_{21}H_{19}F_3N_3O_6^+$, with mass errors from 0.2 to 0.4 ppm, suggesting an addition of O atom (+16 Da), to the parent molecular ion. CID of the molecular ions of M23 resulted in major ions at m/z 448, 423, 307, and 289. CID of the molecular ions of M21 and M54 resulted in major ions at m/z 448, 423, 323, 305, and 289. Accurate mass measurement of these product ions confirmed their chemical formulas. MS spectra suggested that M23, M21, and M54 were the mono hydroxylation metabolites of bictegravir.

Metabolite M20 eluted at 29.92 min on LC-MS chromatogram and had molecular ions at m/z 546. Accurate mass measurement of this ion provided a chemical formula of $C_{21}H_{19}F_3N_3O_9S^+$, with a mass error of 0.3 ppm, suggesting an addition of $SO_4$ moiety to the parent molecular ion. CID of this molecular ion resulted in a major ion at m/z 466, corresponding to a neutral loss of $SO_3$ moiety (−80 Da) from the parent molecular ion. MS3 spectra resulted in fragment ions at m/z 448, 423, 307, and 289. Mass spectra of M20 suggested that it was a sulfate conjugate of the hydroxylated product of bictegravir.

Metabolite Quantitation: LC-Radio-chromatograms of the pooled plasma, urine, and feces samples were obtained. Quantitation of [$^{14}$C]-bictegravir and its metabolites was based on integration of their corresponding peaks on the radio-chromatograms and the radioactivity concentration/radioactive dose recovered in the corresponding sample. The concentrations of bictegravir and its metabolites in the excreta were reported as percent of dose administered. Concentrations measured in the plasma samples were reported as ng equivalent bictegravir/mL.

Radioactivity Recovery: The average extraction recovery from the fecal homogenates and plasma was 95.5% and 100.4%, respectively. The average reconstitution recovery from the dried feces and plasma extract residues was 99.9% and 100.3%, respectively. The recovery from the urine centrifugation process was 100.8%. The recovery from the urine concentration process was 100.6%. The radioactivity recovery from the HPLC column was 99.3%.

Separation and Quantitation of M21 and M22 Metabolites in Pooled Feces

Liquid chromatography was used to separate M21 (hydroxy-bictegravir) and M22 (desfluoro-hydroxy-bictegravir) in pooled feces samples because these two metabolites co-eluted during the metabolite profiling process. M22 eluted as a single peak and the radioactivity was quantified, however, M21 co-eluted with M23. The percent of M21 was calculated by subtraction of M22 from M21/M22 mixture.

M21 and M22 accounted on average for 4.8% and 3.3% of the dose, respectively, through 144 hours postdose in the feces samples pooled per individual subject. In the feces samples pooled per collection interval, M21 and M22 accounted for 2.9% and 4.1% of the dose, respectively, through 144 hours after dose. These analyses indicated that the levels of hydroxy-bictegravir (M21) and desfluoro-hydroxy-bictegravir (M22) were similar, ranging from approximately 3% to 4% of the dose.

Summary of Results

Pharmacokinetics Results: This mass balance study demonstrated that recovery of bictegravir was primarily from feces relative to urine. Metabolism is the major clearance pathway for bictegravir in humans. A total of 20 metabolites of bictegravir were identified by high performance liquid chromatography (HPLC)-MS/TopCount method. Direct glucuronidation, hydroxylation, defluorination, dehydrogenation, and Phase II conjugation of oxidized metabolites were the major metabolic pathways for bictegravir.

In human plasma, [$^{14}$C]bictegravir was the major circulatory radioactive component and M20 (sulfate of hydroxy-bictegravir) and M15 (glucuronide of bictegravir) were the major metabolites in plasma, accounting for approximately 67.9%, 20.1%, and 8.6%, respectively, of the plasma AUC0-72 h of total radioactivity. In human urine, M15 (co-eluted with M58, both direct glucuronides of bictegravir) was the major metabolite (21.4% of dose). The radioactivity in feces samples pooled by time intervals and for individual subjects was accounted for mainly by bictegravir (31% to 34% of dose), the cysteine conjugate of desfluoro-hydroxy-bictegravir (10% to 13% of dose), hydroxy-bictegravir co-eluted with desfluoro-hydroxy-bictegravir (7% to 8% of dose for the co eluted peak), and minor oxidation products. The levels of M21 (hydroxyl-bictegravir) and M22 (desfluoro-hydroxy-bictegravir) were similar, each ranging on average from approximately 3% to 4% of the dose in the M21/M22 mixture in feces from humans.

Example 2: Synthesis and Characterization of M15, M20, and M23

Preparation of M15

Anomeric bromination of 1 with 33% HBr in acetic acid gave bromide 2 in 70% crystallized yield. Treatment of phenol 3 with bromide 2 in the presence of $Ag_2CO_3$ in acetonitrile at 60° C. produced compound 4 in 75% yield after reverse phase chromatography. Deprotection of 4 with triethylamine in methanol/water gave clean conversion to glucuronic acid 5 (M15). The reaction was stopped at 90% conversion since the amount of 3 present in the reaction started to increase. The mixture was purified by reverse phase chromatography with 0.1% TFA in the chromatography solvent. The free acid was isolated after lyophilization, however it contained a significant amount of 3. It was discovered that the free acid 5 was unstable in either neutral or acidic conditions. The triethylamine salt of M15 (5) appeared to be stable. Another batch was purified using the same method as before but the TFA was neutralized with triethylamine before lyophilization. The compound was stable to the conditions but contained a large amount of triethylammonium trifluoroacetate. Not all salt was removed. The material was purified by reverse phase chromatography but without TFA in the solvent. After lyophilization the triethylamine salt of M15 (5) was isolated in high purity and 24% overall yield.

Preparation of M20

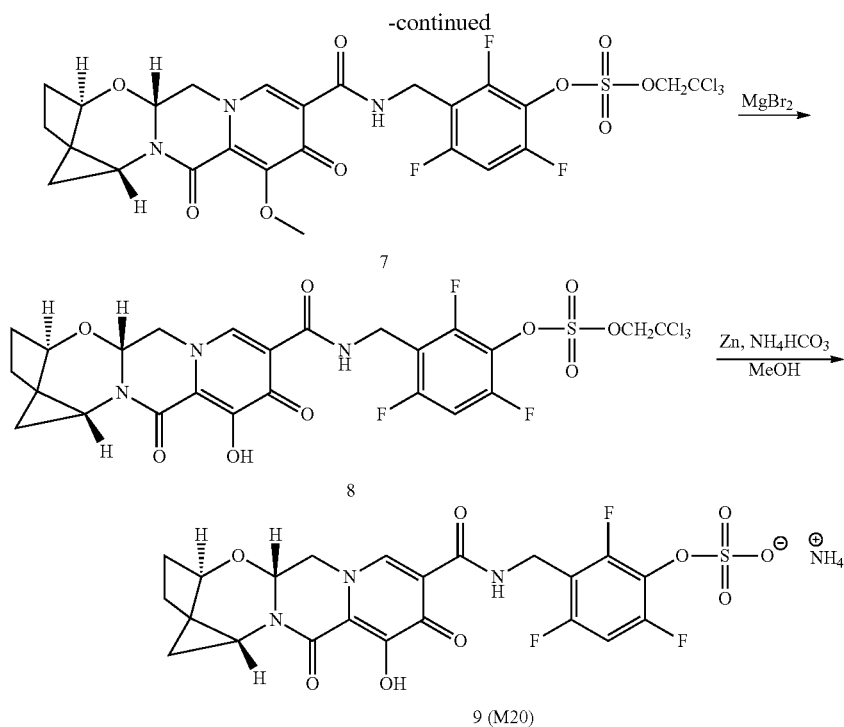

Step 1.

A solution of compound 6 (333 mg, 0.70 mmol), 4-(dimethylamino)pyridine (85 mg, 0.70 mmol), and triethylamine (0.2 mL, 1.44 mmol) in tetrahydrofuran (10 mL) was stirred at room temperature as a solution of 2,2,2-trichloroethyl sulfurochloridate (218 mg, 0.88 mmol) in tetrahydrofuran (2.5 mL) was added over min. After 3.5 h, additional triethylamine (0.1 mL, 0.72 mmol) and 2,2,2-trichloroethyl sulfurochloridate (100 mg, 0.40 mmol) were added. After 1.5 h since addition, the reaction mixture was diluted with ethyl acetate (50 mL) and washed with water (×1), 10% citric acid (×1), water (×1), and brine (×1). After the aqueous fractions were extracted with ethyl acetate (×1), the organic fractions were combined, dried (MgSO$_4$), and concentrated. The residue was purified by CombiFlash (40 g column) eluting 0-10% methanol in dichloromethane to get 458 mg (95%) of compound 7. $^1$H NMR (400 MHz, Chloroform-d) δ 10.40 (t, J=5.8 Hz, 1H), 8.33 (s, 1H), 6.86 (td, J=9.4, 2.2 Hz, 1H), 5.37-5.30 (m, 2H), 4.95 (s, 2H), 4.67 (d, J=5.9 Hz, 2H), 4.63 (s, 1H), 4.19 (dd, J=12.7, 3.9 Hz, 1H), 4.02 (s, 3H), 3.98 (dd, J=12.7, 9.2 Hz, 1H), 2.13-1.95 (m, 4H), 1.83 (qd, J=8.7, 7.6, 3.5 Hz, 1H), 1.57 (ddd, J=12.3, 4.1, 2.9 Hz, 1H). $^{19}$F NMR (376 MHz, Chloroform-d) δ −110.32 (dt, J=9.7, 5.3 Hz), −122.76 (dd, J=9.9, 5.6 Hz), −125.40 (d, J=4.7 Hz). LCMS-ESI$^+$ (m/z): [M+H]$^+$ calculated for $C_{24}H_{22}Cl_3F_3N_3O_9S$: 690.01; found: 690.27.

Step 2.

A solution of compound 7 (255 mg, 0.37 mmol) in acetonitrile (3 mL) was stirred at room temperature as magnesium bromide (180 mg, 0.98 mmol) was added. The resulting suspension was stirred at 50° C. bath. After 30 min, the reaction mixture was stirred at 0° C. as several drops of 0.1 N HCl was added until the insoluble material was dissolved. After the resulting solution was diluted with water (30 mL), the product was extracted with dichloromethane (25 mL×3). The combined extracts were dried (Na$_2$SO$_4$) and concentrated. The residue was purified by CombiFlash (40 g column) eluting 0-15% methanol in dichloromethane to get 178 mg (71%) of compound 8. $^1$H NMR (400 MHz, DMSO-d$_6$) δ 12.46 (s, 1H), 10.44 (t, J=5.9 Hz, 1H), 8.42 (s, 1H), 7.63 (td, J=10.5, 9.9, 2.0 Hz, 1H), 5.43 (dd, J=9.5, 4.0 Hz, 1H), 5.36 (s, 2H), 5.09 (s, 1H), 4.72-4.48 (m, 4H), 4.01 (dd, J=12.7, 9.5 Hz, 1H), 1.93 (s, 4H), 1.83 (d, J=12.1 Hz, 1H), 1.62-1.50 (m, 1H). $^{19}$F NMR (376 MHz, DMSO-d$_6$) δ-110.83 (dd, J=9.8, 5.2 Hz), −124.08 (dd, J=10.9, 5.5 Hz), −126.44. LCMS-ESI$^+$ (m/z): [M+H]$^+$ calculated for $C_{23}H_{20}Cl_3F_3N_3O_9S$: 675.99; found: 676.26.

Step 3.

A solution of compound 8 (50 mg, 0.074 mmol) in methanol (2.5 mL) was stirred at room temperature as ammonium bicarbonate (721 mg, 9.12 mmol) and zinc powder (217 mg, 3.32 mmol) were added. The resulting suspension was stirred at room temperature for 18 h. The reaction mixture was concentrated at room temperature and the residue was dried in vacuum for 30 min. The residual solids was triturated with 0.01 N ammonium bicarbonate (50 mL) with sonication for ~2 min, and the resulting slurry was left at room temperature for 30 min before filtered through celite. After the flask and the celite pad were washed with additional 0.01 N ammonium bicarbonate (10 mL), the combined filtrate and washing were loaded on a reverse phase CombiFlash column (15.5 g), which was previously equilibrated with ~200 mL of 0.01 M ammonium bicarbonate in ~50% aqueous acetonitrile, followed by 0.01 M ammonium bicarbonate in 100% water. The column was eluted with CombiFlash eluting 0-45% solvent B in solvent A (solvent A: 0.01 M ammonium bicarbonate in 100% water; solvent B: 0.01 M ammonium bicarbonate in 80% acetonitrile in water) and the product containing fractions were combined and freeze dried to get 31 mg (75%) of compound 9 (M20) as ammonium salt. LCMS-ESI$^-$ (m/z): [M−H]$^-$ calculated for $C_{21}H_{22}Cl_3F_3N_3O_9S$: 690.01; found: 690.27.

Preparation of M23

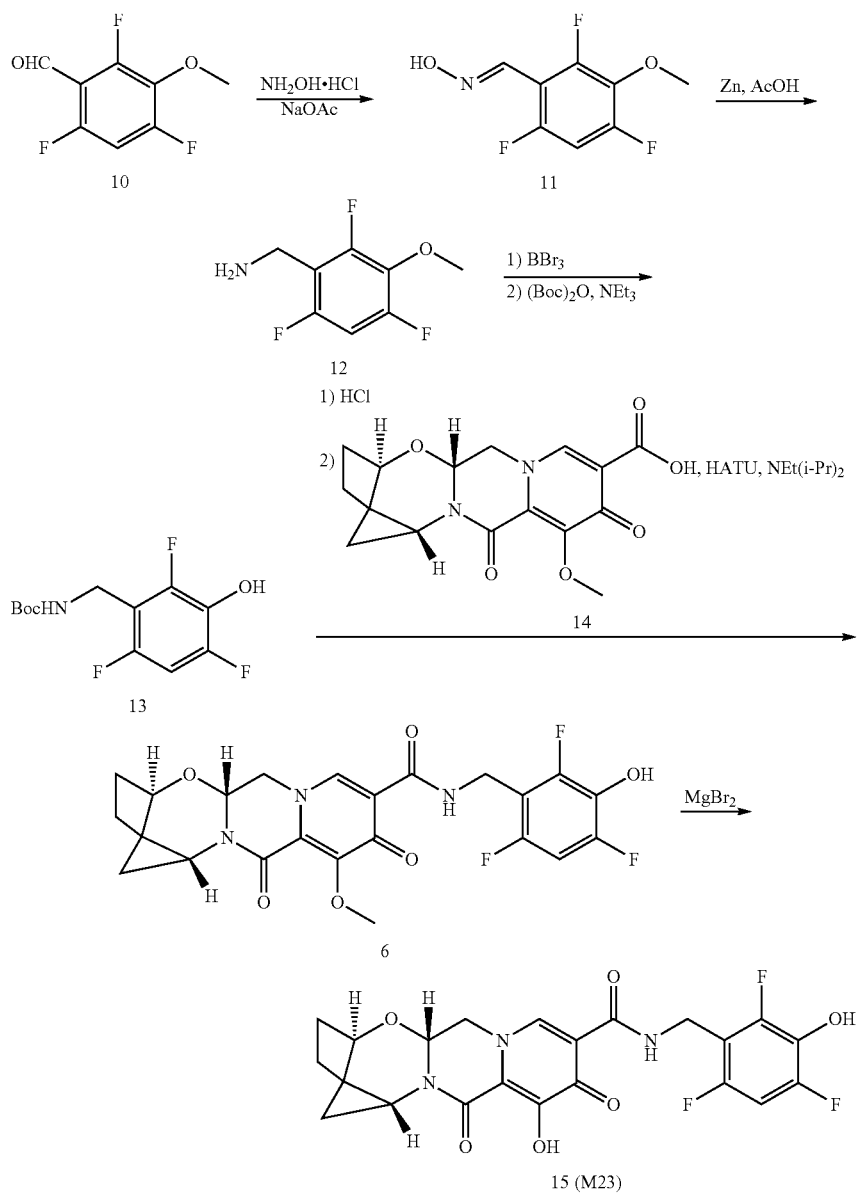

Step 1.

A suspension of 2,4,6-trifluoro-3-methoxybenzaldehyde (10, 2990 mg, 15.7 mmol), hydroxylamine hydrochloride (1352 mg, 19.5 mmol), and sodium acetate (1598 mg, 19.5 mmol) in ethanol (60 mL) was stirred vigorously at room temperature for 2.5 h. The suspension was diluted with water (60 mL) and stirred at ice bath for 1 h. The resulting solid was filtered, washed with cold 50% aqueous ethanol, and dried in vacuum overnight to obtain 2942 mg (91%) of compound 11. $^1$H NMR (400 MHz, DMSO-$d_6$) δ 11.86 (s, 1H), 8.08 (s, 1H), 7.38 (td, J=11.0, 2.2 Hz, 1H), 3.90 (s, 3H). $^{19}$F NMR (376 MHz, DMSO-$d_6$) δ -117.25 (dd, J=10.9, 3.5 Hz), -125.34 (ddd, J=11.9, 8.6, 3.6 Hz), -128.35 (dd, J=8.5, 2.2 Hz). LCMS-ESI$^+$ (m/z): [M+H]$^+$ calculated for $C_8H_7F_3NO_2$: 206.04; found: 206.00.

Step 2.

A solution of compound 11 (601 mg, 0.98 mmol) in acetic acid (6 mL) was stirred at 65° C. while zinc powder (1500 mg, 7.65 mmol) was added portionwise over 30 min. After addition, the mixture was stirred at 65° C. After 1.5 h, the reaction mixture was filtered and the filtrate was concentrated to dryness. The residue was dissolved in water and washed with diethyl ether (×1). After the organic fraction was extracted with water with 2 drops of acetic acid, the two aqueous fractions were combined, diluted with saturated aqueous NaHCO$_3$ until it became neutral, and extracted with ethyl acetate (~25 mL×5). The extracts were combined, dried (MgSO$_4$), and concentrated to get 440 mg (79%) of the corresponding crude amine 12. LCMS-ESI$^+$ (m/z): [M+H]$^+$ calculated for $C_8H_9F_3NO$: 192.06; found: 191.86.

Step 3.

A solution of the above amine 12 (440 mg, 2.30 mmol) in dichloromethane (1.5 mL) was stirred at room temperature as 1 M boron tribromide in dichloromethane (7 mL, 7 mmol) was added. After 2 h, additional 1 M boron tribromide in dichloromethane (1 mL, 1 mmol) was added to the solution. After 2 h since addition, the reaction mixture was cooled at ice bath and methanol (15 mL) was added slowly. The solution was concentrated and the residual oil was dissolved with methanol (~15 mL) before concentration, which was repeated 4 times. The resulting residue was dissolved in methanol, and stirred in ice bath before addition of triethylamine (1.5 mL, 10.76 mmol) followed by di-tert-butyl dicarbonate (593 mg, 2.72 mmol). The resulting mixture was stirred at 0° C. for 2 h and then at room temperature overnight. After the resulting solution was concentrated, the residue was dissolved in ethyl acetate (~30 mL) and water (~30 mL), and acidified with 10% citric acid. Two fractions were separated and the aqueous fraction was extracted with ethyl acetate (×1). After the organic fractions were washed with brine (×1), the combined organic fractions were dried (MgSO$_4$) and concentrated. The residue was purified by CombiFlash (40 g column) eluting 0-100% EA in hexane to get 530 mg (83%) of compound 13. $^1$H NMR (400 MHz, Chloroform-d) δ 6.70 (ddd, J=10.3, 9.4, 2.3 Hz, 1H), 5.62 (br, 1H), 4.89 (s, 1H), 4.37 (d, J=5.8 Hz, 2H), 1.44 (s, 9H). $^{19}$F NMR (376 MHz, Chloroform-d) δ-125.17--126.42 (m, 1F), -132.92--134.28 (m, 1F), -137.39 (m, 1F). LCMS-ESI$^+$ (m/z): [M-C$_4$H$_8$+H]$^+$ calculated for C$_8$H$_7$F$_3$NO$_3$: 222.04; found: 221.95.

Step 4.

A solution of compound 13 (530 mg, 1.91 mmol) in dichloromethane (4.8 mL) was stirred at 0° C. as 4 M HCl in dioxane (4.8 mL, 19.2 mmol) was added. After addition, the mixture was stirred at room temperature. After 1.75 h, the reaction mixture was concentrated and the residual white solid was co-evaporated with toluene (~20 mL×2) before being dried in vacuo overnight to obtain 399 mg (98%) of the crude amine hydrochloride salt.

A suspension of the acid 14 (600 mg, 1.87 mmol), the above amine HCl salt (399 mg, 1.87 mmol), and 2-(7-aza-1H-benzotriazole-1-yl)-1,1,3,3-tetramethyluronium hexafluorophosphate (HATU, 748 mg, 1.97 mmol) in dichloromethane (12 mL) was stirred at room temperature as N,N-diisopropylethylamine (1.65 mL, 9.47 mmol) was added. After 15 min, additional HATU (712 mg, 1.87 mmol), N,N-diisopropylethylamine (1.65 mL, 9.47 mmol), and DMF (3 m) were added to the mixture. After 15 min since the addition, the solution was concentrated to remove the most of dichloromethane and the residue was diluted with methanol (25 mL). After the resulting solution was stirred at room temperature for 1 h, it was concentrated to remove most of the methanol, and diluted with ethyl acetate (~70 mL) before washing with aqueous ammonium chloride (×2), aqueous NaHCO$_3$ (×2), and brine (×1). After the aqueous fractions were extracted with ethyl acetate (~75 mL×1), the organic fractions were combined, dried (MgSO$_4$), and concentrated. The residue was purified by CombiFlash (80 g column) eluting with 0-11% methanol in dichloromethane to get 647 mg (72%) of compound 6. $^1$H NMR (400 MHz, Chloroform-d) δ 10.32 (t, J=5.8 Hz, 1H), 8.33 (s, 1H), 7.25 (s, 1H), 6.65 (ddd, J=10.7, 9.4, 2.2 Hz, 1H), 5.36 (dd, J=9.6, 3.7 Hz, 2H), 4.68-4.53 (m, 3H), 4.25 (dd, J=12.8, 3.8 Hz, 1H), 4.02 (dd, J=13.0, 9.9 Hz, 1H), 3.99 (s, 3H), 2.14-1.93 (m, 4H), 1.91-1.78 (m, 1H), 1.61-1.52 (m, 1H). $^{19}$F NMR (376 MHz, Chloroform-d) δ-125.85 (d, J=9.2 Hz), -132.78 (t, J=10.6 Hz), -136.03 (d, J=10.7 Hz). LCMS-ESI$^+$ (m/z): [M+H]$^+$ calculated for C$_{22}$H$_{21}$F$_3$N$_3$O$_6$: 480.14; found: 480.27.

Step 5.

To a solution of compound 6 (300 mg, 0.63 mmol) in acetonitrile (~10 mL) was added magnesium bromide (299 mg, 1.63 mmol) at room temperature and the resulting mixture was stirred at 50° C. bath for 20 min. The reaction mixture was concentrated and the residue was triturated with water (100 mL) and dichloromethane (100 mL). The suspension was stirred while in an ice bath and 1 N HCl was added to make the mixture strongly acidic (pH, ~2). After the insoluble product was filtered, the two fractions were separated and the aqueous fraction was extracted with dichloromethane (~100 mL×2). The combined organic fractions were dried (MgSO$_4$), concentrated, and purified by CombiFlash (24 g column) eluting 0-20% methanol in dichloromethane. The obtained product was combined with the previously obtained solid product, dissolved in methanol, filtered to remove debris, and concentrated to get amorphous solid. The amorphous solid was crystalized in acetonitrile (~10 mL) and the crystal formed was filtered, washed with cold acetonitrile, and dried in vacuum to get 209 mg (72%) of compound 15 (M23). $^1$H NMR (400 MHz, DMSO-d$_6$) δ 12.44 (s, 1H), 10.33 (t, J=5.7 Hz, 1H), 10.11 (s, 1H), 8.44 (s, 1H), 7.27-7.01 (m, 1H), 5.44 (dd, J=9.6, 4.1 Hz, 1H), 5.09 (d, J=3.8 Hz, 1H), 4.67 (dd, J=12.9, 4.1 Hz, 1H), 4.60 (s, 1H), 4.59-4.43 (m, 2H), 4.02 (dd, J=12.7, 9.6 Hz, 1H), 1.93 (d, J=5.1 Hz, 4H), 1.84 (d, J=12.1 Hz, 1H), 1.57 (dt, J=12.2, 3.5 Hz, 1H). $^{19}$F NMR (376 MHz, DMSO-d$_6$) δ-127.13, -131.52 (t, J=11.2 Hz), -134.59 (d, J=11.4 Hz). LCMS-ESI$^+$ (m/z): [M+H]$^+$ calculated for C$_{21}$H$_{19}$F$_3$N$_3$O$_6$: 466.12; found: 466.26.

Example 3: Confirmation of Chemical Structure of M15

General Methods

All times, centrifuge speeds, temperatures, and volumes are approximate due to the normal accuracy constraints of laboratory equipment. Unless otherwise noted, centrifugation was conducted as outlined in the following table.

TABLE 1

| Matrix | Force | Time (Minutes) | Temperature |
| --- | --- | --- | --- |
| Plasma[a] | 2800 × g | 10 | Ambient |
| Plasma[b] | 1400 × g | 10 | Ambient | g Gravity.
[a]Extraction step.
[b]Reconstitution step.

Plasma

Plasma samples used in this Example were stored at approximately -70° C. before and after analysis. Plasma samples obtained from male human subjects at 8 hours post-dose were pooled, including 0.4 g of each sample by weight. The radioactivity in the pooled sample was determined by liquid scintillation counting (LSC).

Approximately 1 g of the pooled plasma sample was combined with 3 mL of 0.2% (v/v) formic acid (FA) in acetonitrile (ACN), sonicated, vortex mixed, centrifuged, and the supernatant was removed. The extraction was repeated, and the respective supernatants were combined. Duplicate aliquots were analyzed by LSC to determine the extraction recovery, which was 96.6%.

The combined supernatants were evaporated to dryness under nitrogen and reconstituted in 350 μL of reverse osmosis water: 0.2% (v/v) formic acid (FA) in acetonitrile (ACN): methanol: (4:1:2, v:v:v). Samples were sonicated, vortex mixed, centrifuged, and duplicate aliquots were analyzed by LSC to determine the reconstitution recovery, which was 104%. The reconstituted sample was analyzed by LC-MS, with eluent fractions collected at 10 second intervals into 96-well plates containing solid scintillant. Radioactivity in each well was determined using TopCount analysis, and a radiochemical profile was generated based on radioactivity counts.

Co-Chromatography of a Plasma Sample with M15 Standard

An additional plasma sample was prepared by combining 40 μL of the pooled 8 hour plasma sample with 40 μL of the standard solution of M15 (500 ng/mL). The sample was analyzed by LC-MS using the following instrumentation and conditions:

| LC-MS Instrumentation | |
|---|---|
| Autosampler: | Acquity Sample Manager FTN (10° C.) |
| Binary pump: | Acquity I-Class Binary Solvent Manager |
| Column oven: | Acquity Column Manager (25° C.) |
| Fraction collector: | LEAP Technologies PAL HTS-xt (15° C.) |
| Mass spectrometer: | Vion IMS Q-TOF |

| LC-MS Conditions | | | |
|---|---|---|---|
| Ionization interface: | Positive lock mass electrospray interface | | |
| HPLC column: | Phenomenex, Luna C18(2), 4.6 × 250 mm, 5 μm | | |
| Guard column: | Phenomenex, KrudKatcher Ultra | | |
| Mobile phase A: | 0.1% (v/v) formic acid in water | | |
| Mobile phase B: | 0.1% (v/v) formic acid in acetonitrile | | |
| | Time (minutes) | % A | % B |
| Gradient: | 0.0 | 85 | 15 |
| | 0.1 | 85 | 15 |
| | 4.0 | 85 | 15 |
| | 40.0 | 60 | 40 |
| | 44.0 | 0 | 100 |
| | 54.0 | 0 | 100 |
| | 56.0 | 85 | 15 |
| | 64.0 | 85 | 15 |
| Flow rate: | 1.0 mL/minute; split ratio 1:3, mass spectrometer:fraction collector | | |

| LC-MS Conditions | |
|---|---|
| Survey scan: | m/z 50-1000 at 200 ms scan time |
| Auto $MS^2$ scans: | m/z 50-1000 at 300 ms scan time |
| Capillary voltage: | 3500 V |
| Drying gas temperature: | 450° C. |
| Source temperature: | 120° C. |

Metabolite Identification

Samples of human plasma were analyzed by using LC-MS, and metabolite M15 was confirmed to be the same component as the standard. The structure, parent mass, and characteristic product ions of M15 from analysis of a plasma sample are presented in Table 2. A summary of representative accurate mass data is presented in Table 3.

Figure 2:
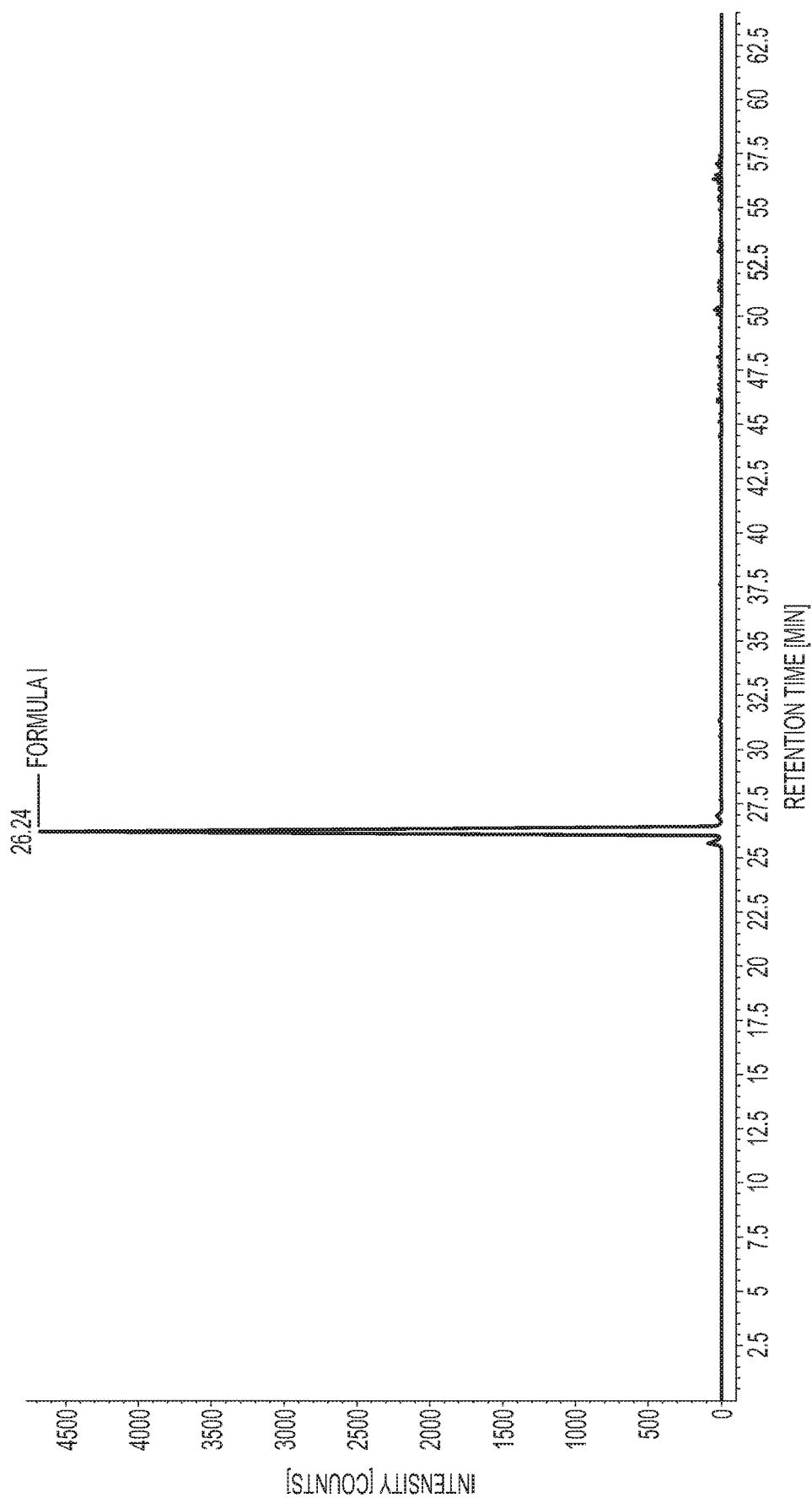
FIG. 2 shows an extracted ion chromatogram of M15 from analysis of a standard solution M15.

An extracted ion chromatogram for M15 in a standard solution is presented in FIG. 2. A radiochromatogram and extracted ion chromatogram for M15 in a pooled plasma sample is presented in FIG. 3. Extracted ion chromatograms comparing the standard, pooled plasma sample, and co-injection sample are presented in FIG. 4. To confirm that M15 and the standard M15 were the same component, the M15 standard solution and the human plasma sample were analyzed separately and were co-injected. The retention times of M15 were 26.24 and 26.28 minutes in the M15 standard solution and human plasma samples, respectively, when analyzed individually (FIG. 1 and FIG. 2). When the M15 standard solution and plasma sample were co-injected, a single peak was observed with a retention time of 26.28 minutes, as shown in FIG. 4.

Figure 5A:
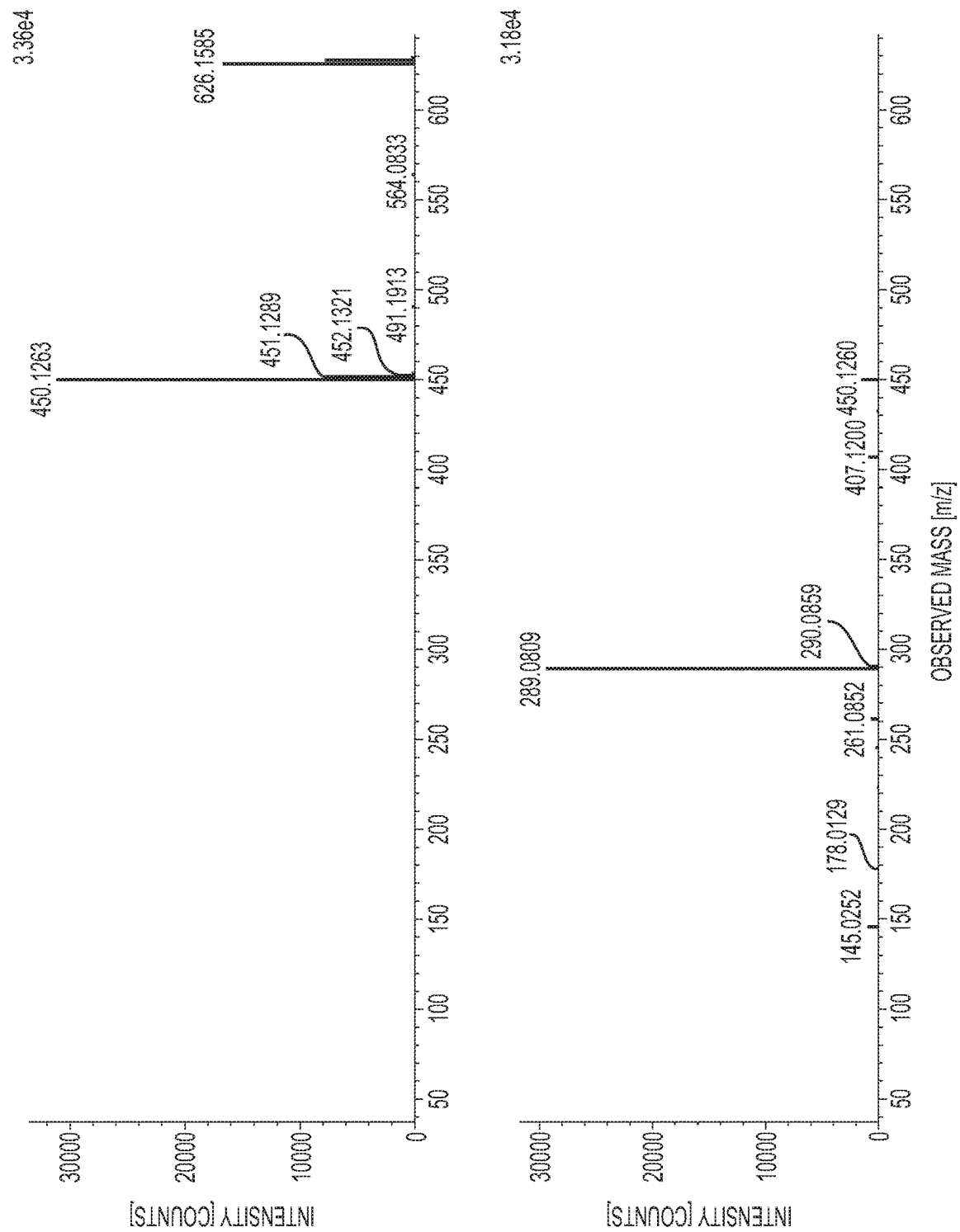
FIG. 5A shows MS precursor and MS/MS product ion mass spectra (m/z 626) of M15 from analysis of a standard solution of M15.
Figure 5B:
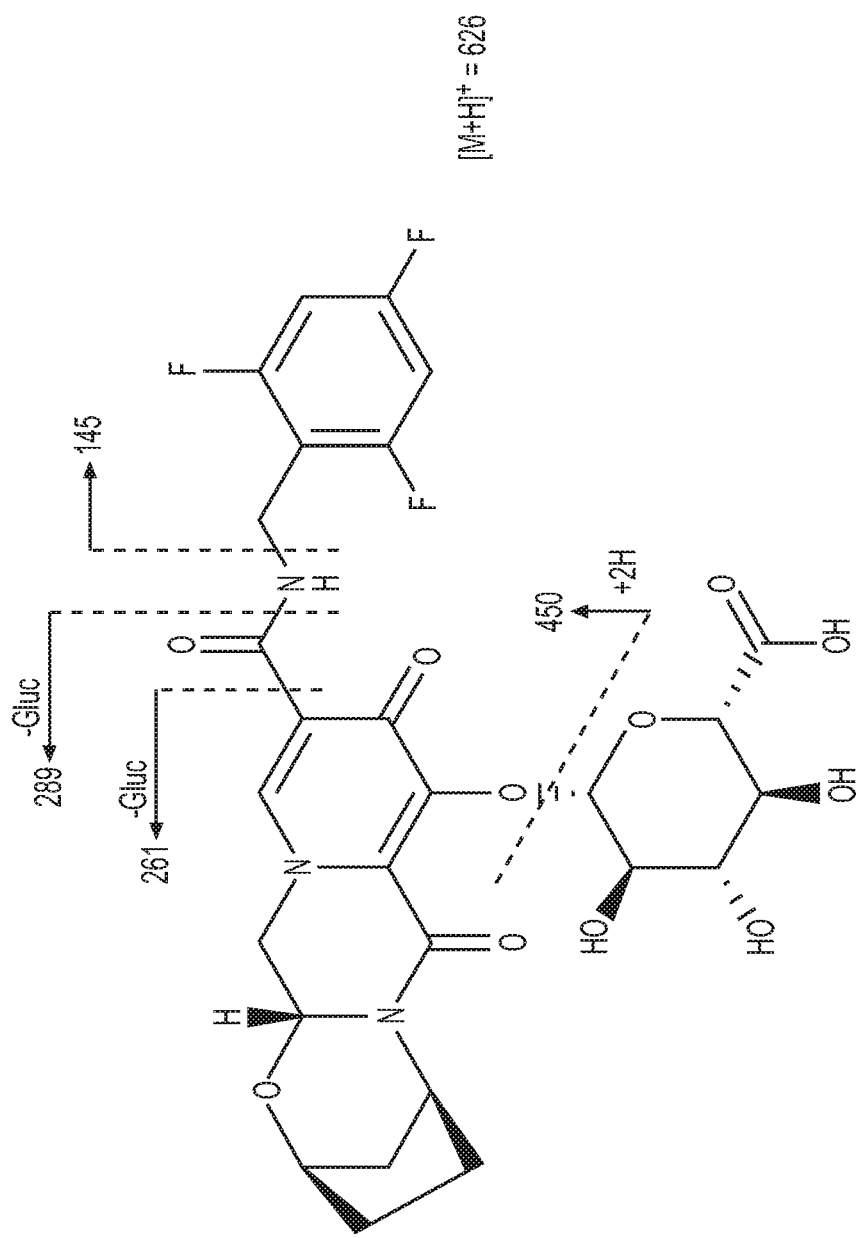
FIG. 5B shows the proposed structure and proposed fragmentation pattern of M15.
Figure 6:
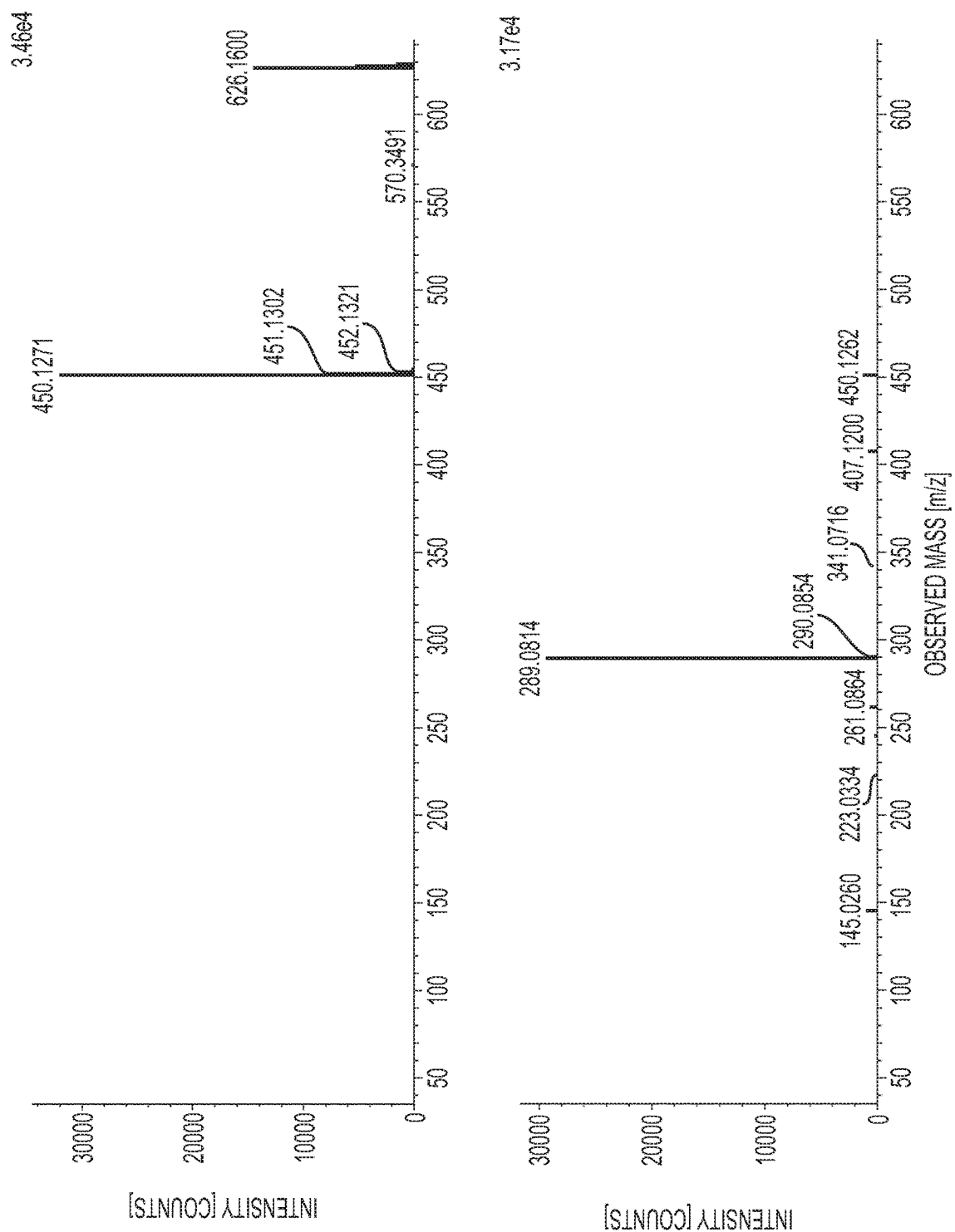
FIG. 6 shows MS precursor and MS/MS product ion mass spectra (m/z 626) of metabolite M15 from analysis of an 8-hour pooled plasma sample obtained after a single oral dose of [$^{14}$C]bictegravir to male human subjects (100 mg, 100 μCi).

Representative MS precursor and MS/MS product ion mass spectra of M15, obtained from analysis of a standard solution of M15, are shown in FIG. 5. The MS precursor ion mass spectrum shows the protonated molecular ion at m/z 626. The MS/MS product ion mass spectrum shows fragment ions at m/z 450, 289, 261, and 145. Representative MS precursor and MS/MS product ion mass spectra of metabolite M15, obtained from analysis of a study sample, are shown in FIG. 6, and the MS/MS product ion mass spectrum is virtually identical to that of the standard. The elemental composition of metabolite M15 was confirmed using accurate mass analysis and is shown in Table 3.

TABLE 2

| Metabolite Designation | Retention Time (Minutes) | [M + H]$^+$ | Proposed Metabolite Identification | Characteristic Product Ions (m/z) | Matrix |
|---|---|---|---|---|---|
| M15 | 26.28[a] | 626 | 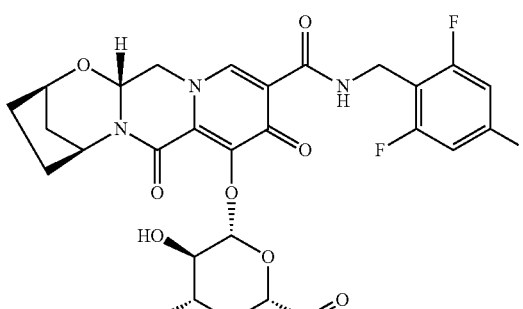 | 450, 289, 261, 145 | Plasma |

Figure 3:
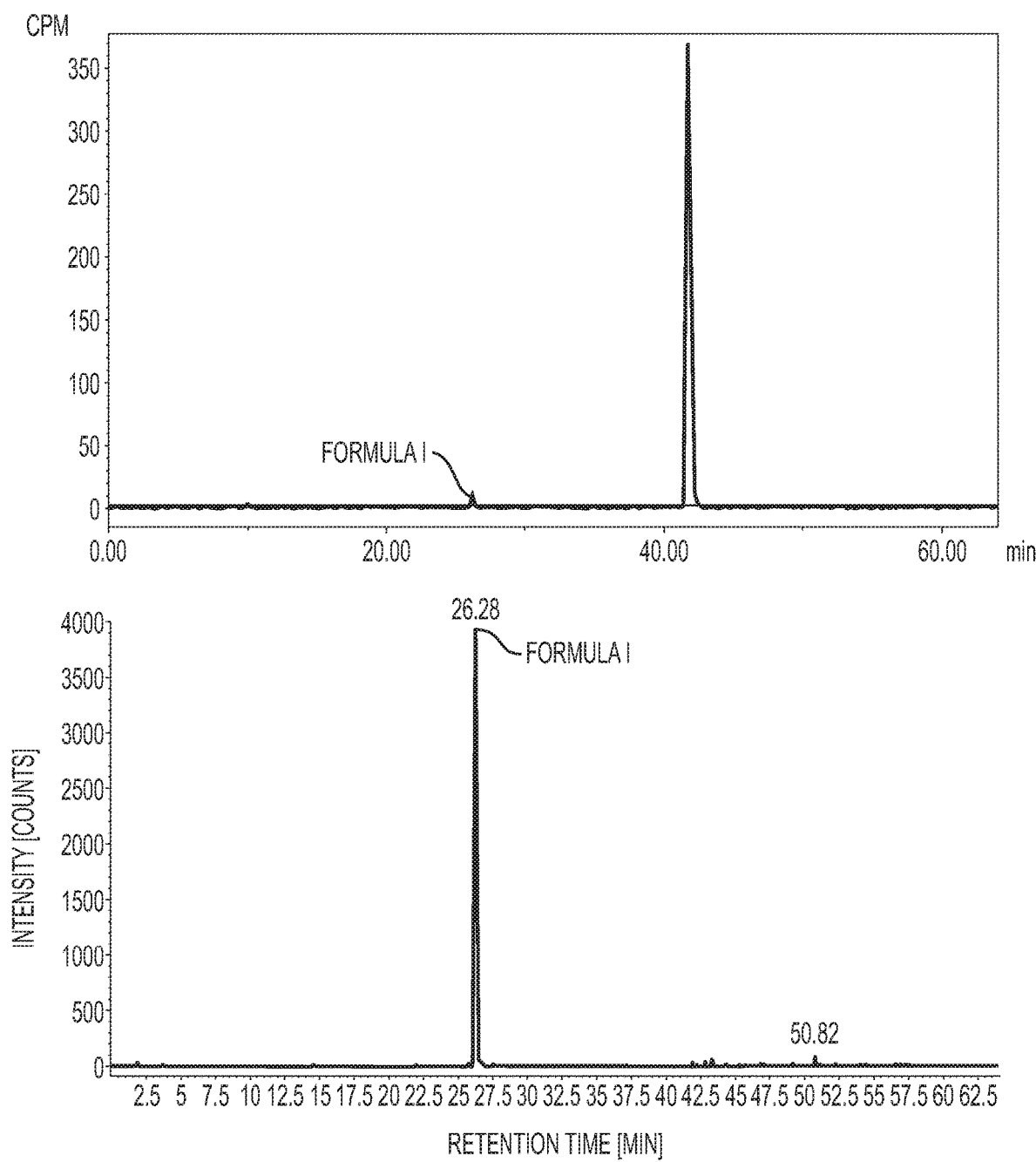
FIG. 3 shows a radiochromatogram and extracted ion chromatogram of metabolite M15 from analysis of an 8-hour pooled plasma sample obtained after a single oral dose of [$^{14}$C]bictegravir to male human subjects (100 mg, 100 μCi).
Figure 4:
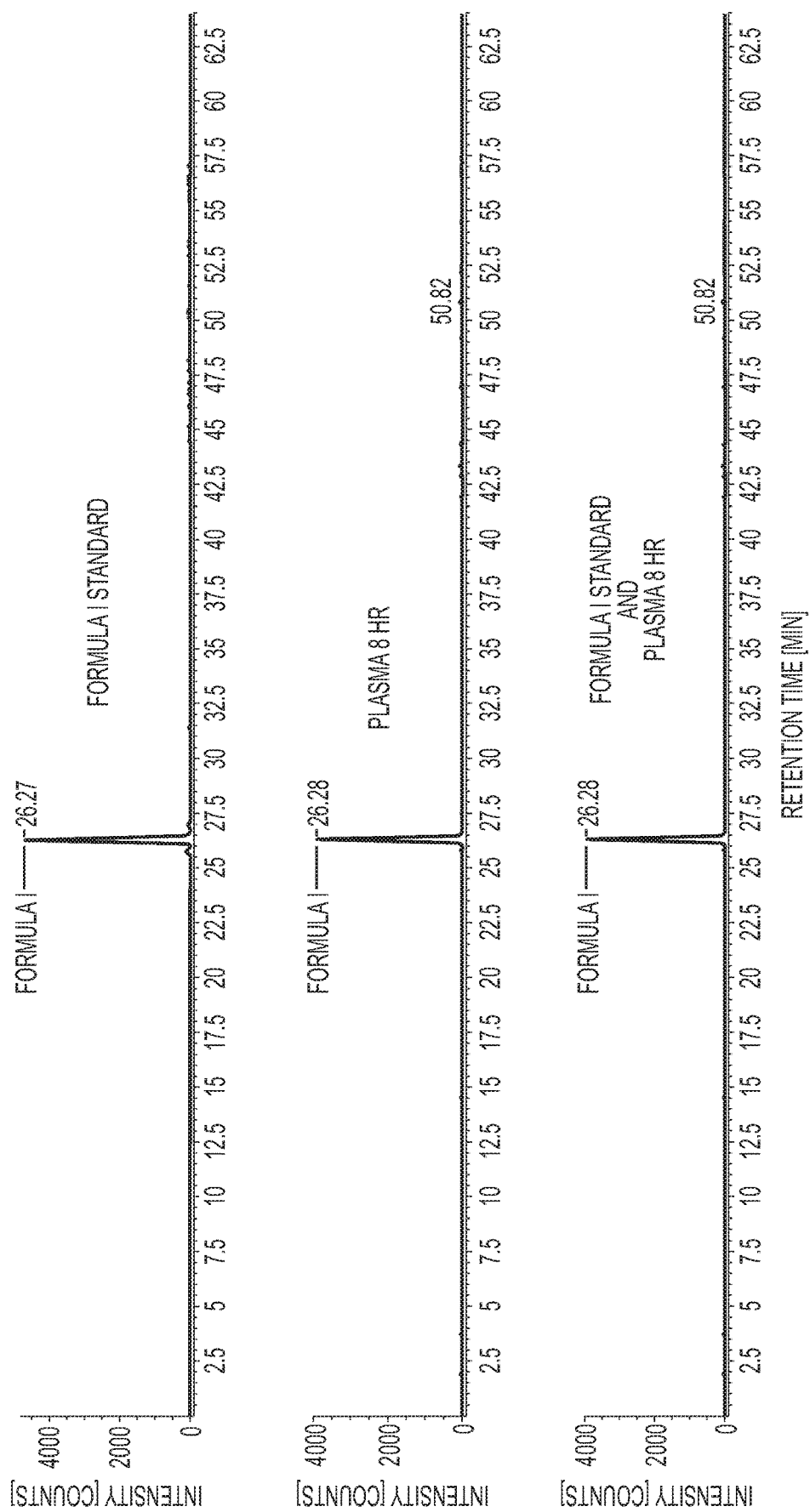
FIG. 4 shows extracted ion chromatograms from individual and co-injection of a standard solution of M15 with an 8-hour pooled plasma sample obtained after a single oral dose of [$^{14}$C]bictegravir to male human subjects (100 mg, 100 μCi).

[a]Retention time from analysis of a plasma sample (Figure 3).

TABLE 3

| Metabolite Designation | Measured Mass | Theoretical Mass | Proposed Formula | Δ mDa | Δ ppm |
|---|---|---|---|---|---|
| M15 | 626.1600 | 626.1592 | $C_{27}H_{27}F_3N_3O_{11}^+$ | 0.80 | 1.3 |

Δ +L6 = (Measured mass − Theoretical Mass) * 1000.
Δ +L6 Δ ppm = (Δ mDa/Theoretical Mass) * 1000.

Example 4: Confirmation of Chemical Structure of M20

All times, centrifuge speeds, temperatures, and volumes are approximate due to the normal accuracy constraints of laboratory equipment. Unless otherwise noted, centrifugation was conducted at a speed of approximately 2800×g for 10 minutes at room temperature.

Solutions

The following solution was used for sample preparation procedures.

| Solution Name | Composition |
|---|---|
| Standard Solution of M20 | 2 μg/mL in reverse osmosis water:methanol:0.2% (v/v) formic acid in acetonitrile (4:2:1, v/v/v) |

Plasma

Plasma samples obtained from male human subjects at 8 hours post-dose were pooled, including 200 μL of each sample. The radioactivity in each pooled sample was determined by liquid scintillation counting (LSC).

The pooled plasma sample was combined with 3 mL of 0.2% (v/v) formic acid (FA) in acetonitrile (ACN), sonicated, vortex mixed, centrifuged, and the supernatants were removed. The extraction was repeated, and the respective supernatants were combined. Duplicate aliquots were analyzed by LSC to determine the extraction recovery, which was 98.6%. The combined supernatants were evaporated to dryness under nitrogen and reconstituted in 350 μL of reverse osmosis water:methanol:0.2% (v/v) FA in ACN (4:2:1, v:v:v). Samples were sonicated, vortex mixed, centrifuged, and duplicate aliquots were analyzed by LSC to determine the reconstitution recovery, which was 100%. The reconstituted sample was analyzed by LC-MS with eluent fractions collected at 10-second intervals into 96-well plates containing solid scintillant. Radioactivity in each well was determined using TopCount analysis, and a radiochemical profile was generated based on radioactivity counts.

Co-Chromatography of Plasma Sample with M20 Standard

An additional sample was prepared by combining 100 μL of the reconstituted 8-hour pooled plasma sample with 50 μL of the standard solution of M20. The resulting sample contained approximately 1:1 ratio of bictegravir:M20. The sample was analyzed by LC-MS using the following instrumentation and conditions.

| LC-MS Instrumentation | |
|---|---|
| Controller: | Shimadzu/Prominence CBM-20A |
| Pumps: | Shimadzu/Nexera LC-30AD |
| Autoinjector: | Shimadzu/Nexera SIL-30ACMP (15° C.) |
| Column Oven: | Shimadzu/Prominence CTO-20AC (25° C.) |
| Degasser: | Shimadzu/Prominence DGU-20A5R |
| Mass spectrometer: | Thermo Fisher Scientific Q Exactive |
| Fraction collector: | Leap Technologies PAL HTC-xt (15° C.) |

| LC-MS Conditions | | | |
|---|---|---|---|
| Ionization interface: | Positive heated electrospray interface (HESI) | | |
| HPLC column: | Phenomenex, Luna C18 (2), 4.6 × 250 mm, 5 μm | | |
| Guard column: | Phenomenex C18, 3 × 4 mm | | |
| Mobile phase A: | 0.1% (v/v) formic acid in water | | |
| Mobile phase B: | 0.1% (v/v) formic acid in acetonitrile | | |
| | Time (minutes) | % A | % B |
| Gradient: | 0.0 | 85 | 15 |
| | 4.0 | 85 | 15 |
| | 40.0 | 60 | 40 |
| | 44.0 | 0 | 100 |
| | 54.0 | 0 | 100 |
| | 56.0 | 85 | 15 |
| | 64.0 | 85 | 15 |
| Flow rate: | 1.00 mL/minute; split ratio 25:75 mass spectrometer:fraction collector | | |
| Survey scan: | m/z 150-900 at 70,000 resolution | | |
| Dependent Scans: | $MS^2$ at 17,500 resolution | | |
| Source Voltage: | +4.5 kV | | |
| S-Lens RF level | 40 | | |

Metabolite Identification

The structure, parent mass, and characteristic product ions of M20 as a standard and in a plasma sample are presented in Table 5. A summary of representative accurate mass data is presented in Table 6.

Figure 7:
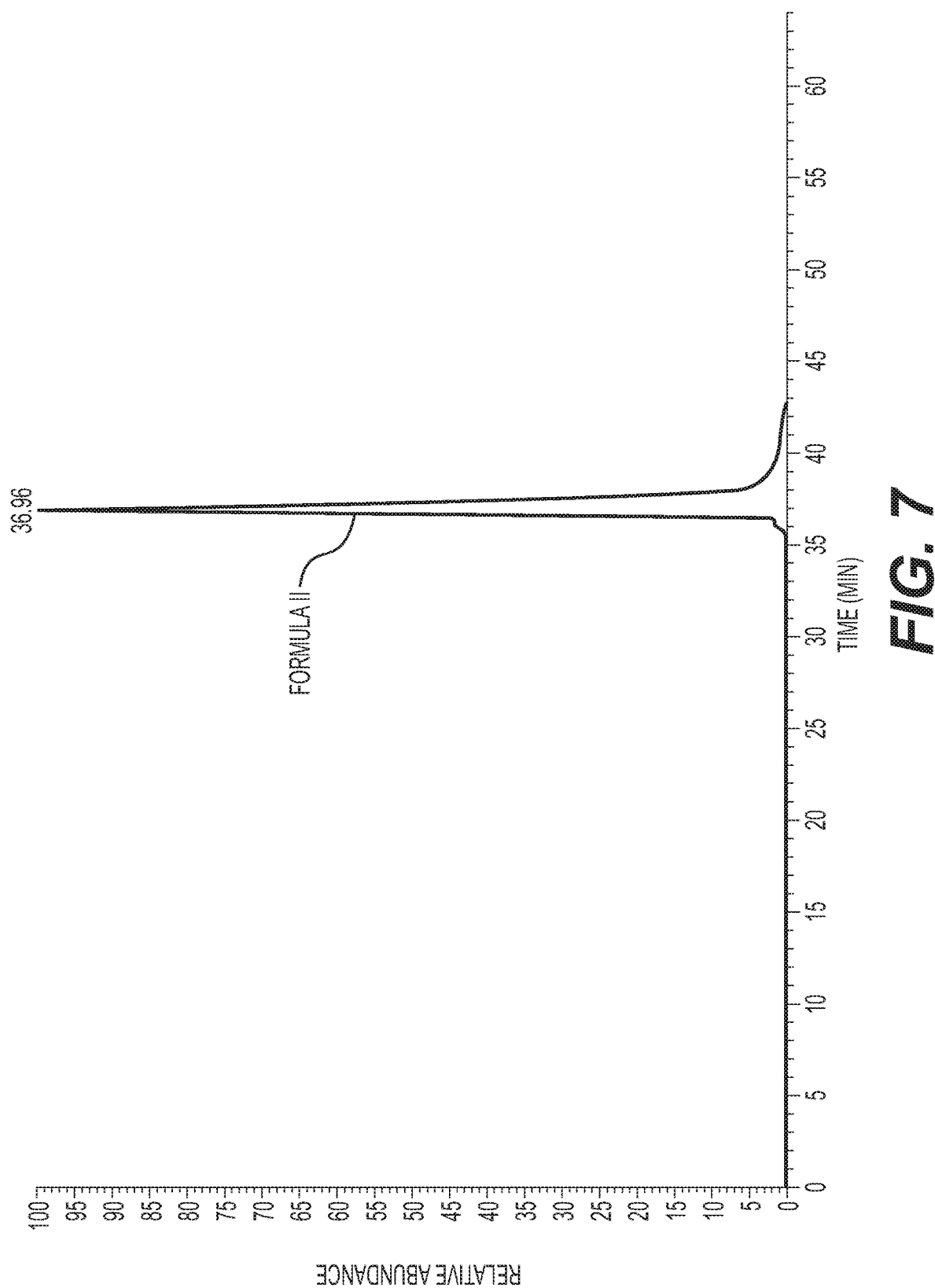
FIG. 7 shows an extracted ion chromatogram from analysis of a standard solution of M20.

An extracted ion chromatogram for M20 in a standard solution is presented in FIG. 7. An extracted ion chromatogram and a radiochromatogram for M20 in a pooled plasma sample are presented in FIG. 8. Extracted ion chromatograms comparing the standard, pooled plasma sample, and co-injection sample are presented in FIG. 9. To confirm that the M20 of the standard solution and M20 were the same component, the M20 standard solution and the human plasma sample were analyzed separately and were co-injected. The retention times of M2 were 36.96 and 37.94 minutes in the M20 standard solution and human plasma samples, respectively, when analyzed individually (FIG. 9). When the M20 standard solution and plasma sample was co-injected, a single peak was observed with a retention time of 37.29 minutes.

Figure 10A:
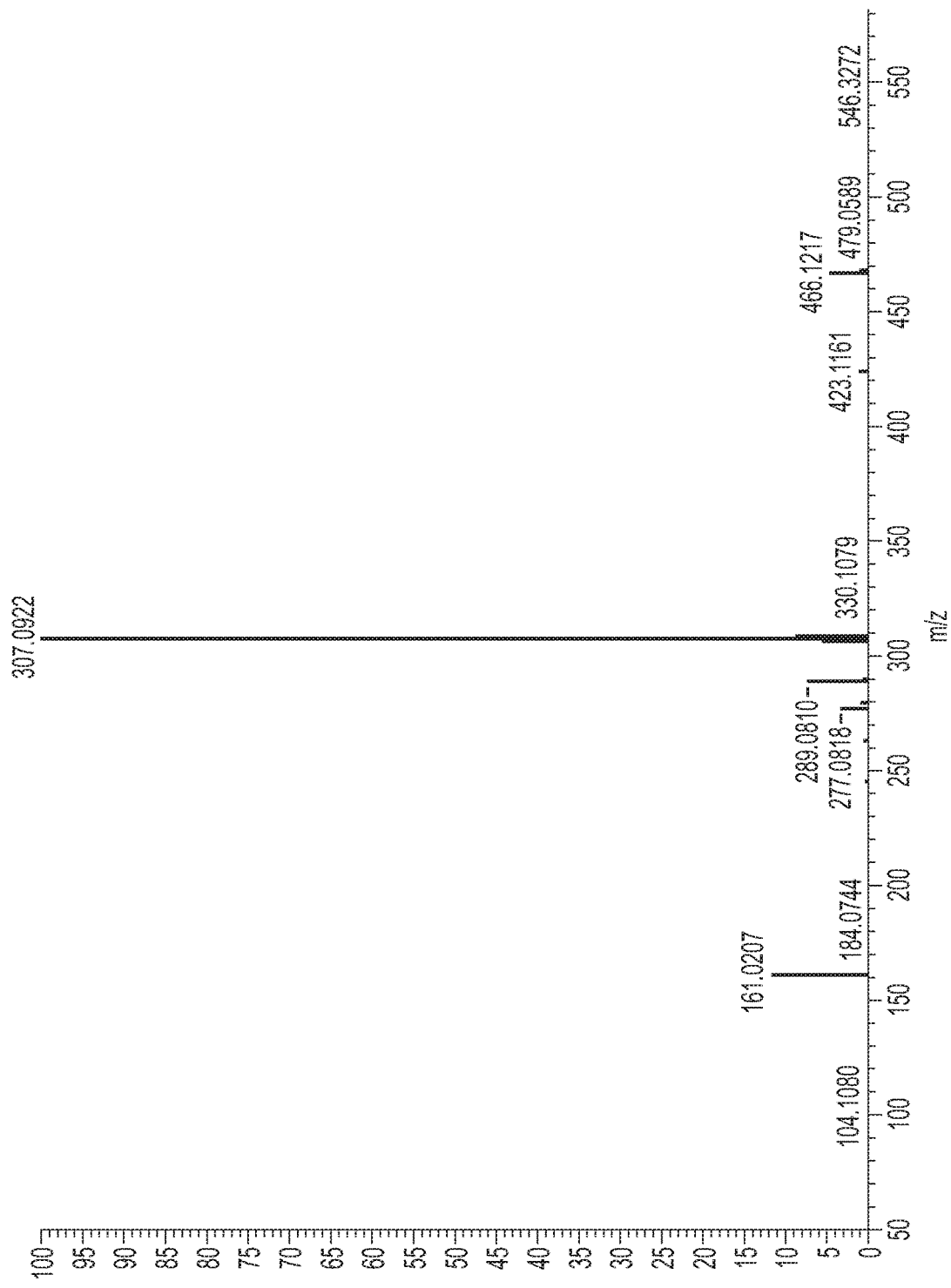
FIG. 10A shows product ion (m/z 546) mass spectrum of M20 from analysis of a standard solution of M20.
Figure 10B:
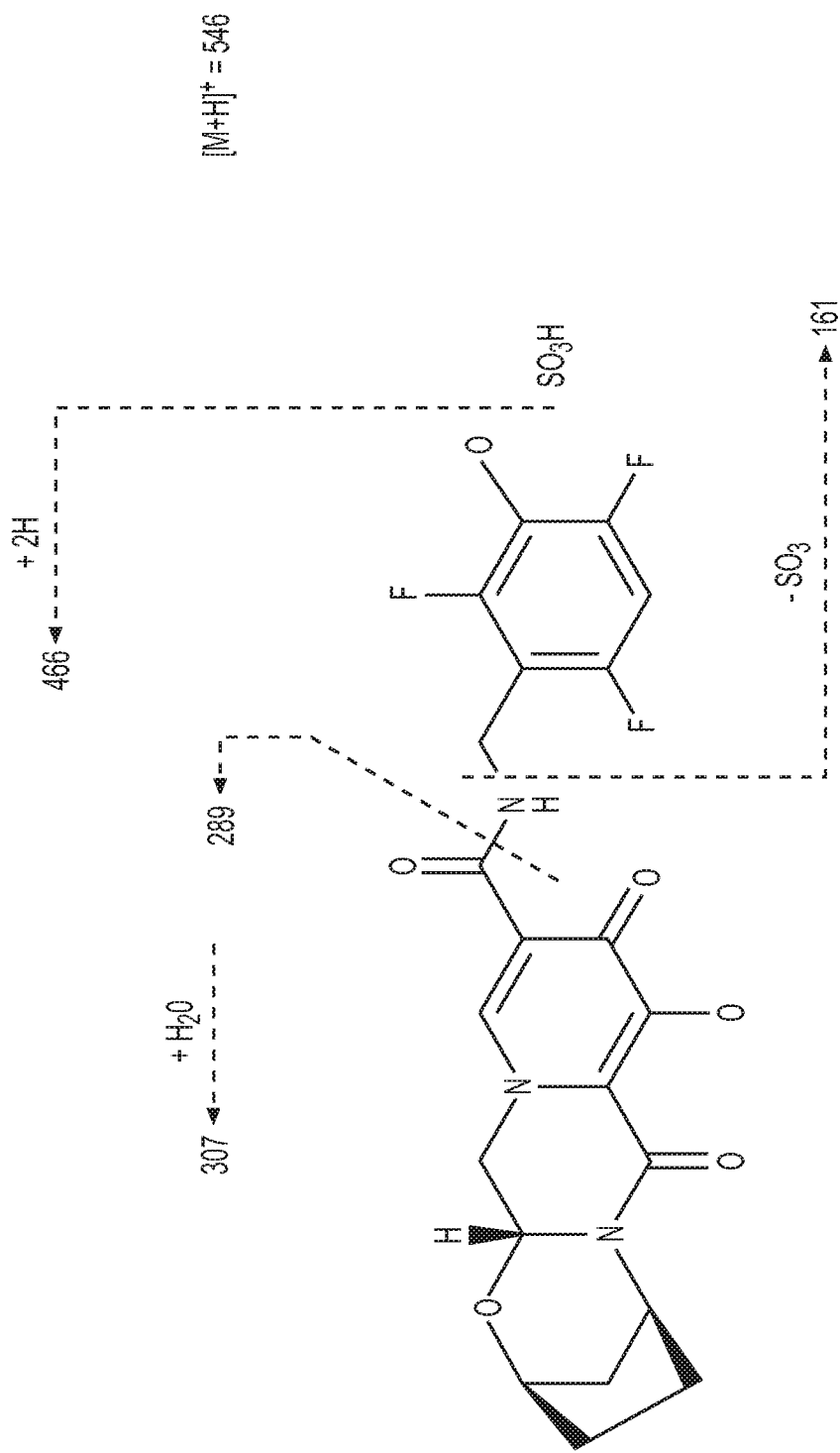
FIG. 10B shows the proposed structure and proposed fragmentation pattern of M20.
Figure 11:
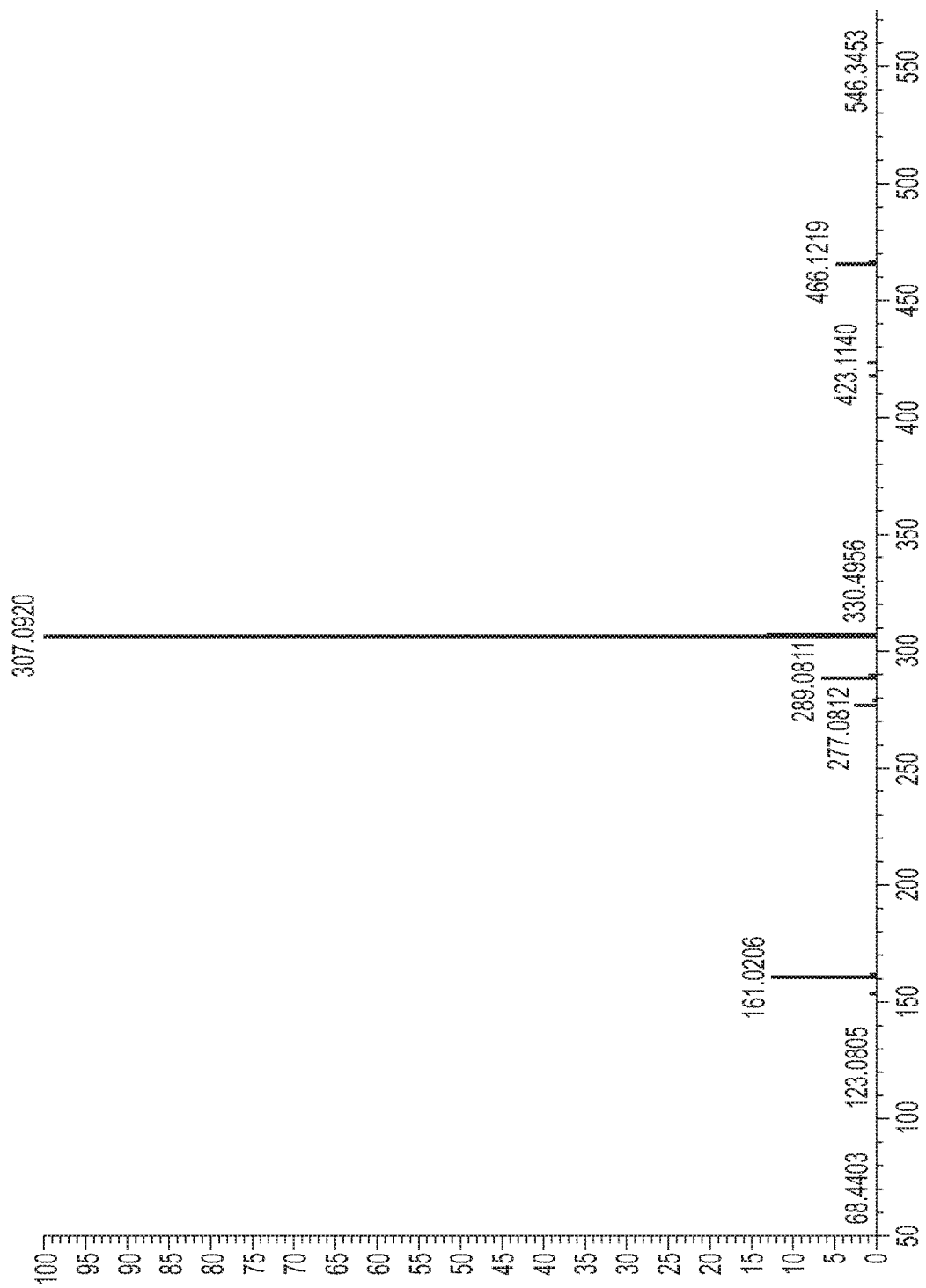
FIG. 11 shows product ion (m/z 546) mass spectrum of M20 from analysis of an 8-hour pooled plasma sample obtained after administration of a single oral dose of [$^{14}$C] bictegravir to male human subjects (100 mg, 100 μCi).

The protonated molecular ion of M20 was observed at m/z 546 (data not shown). A representative product ion mass spectrum of M20 obtained from analysis of a standard solution of M20 is shown in FIG. 10. The mass spectrum showed product ions at m/z 466 (loss of $SO_3$), 307 (m/z 289 plus water), 289, and 161. A representative product ion mass spectrum of M20 obtained from the human plasma sample is shown in FIG. 11, and is virtually identical to that of the standard. The elemental composition of M20 was confirmed using accurate mass analysis, as shown in Table 6.

TABLE 5

| Metabolite Designation | Retention Time (Minutes) | [M + H]+ | Proposed Metabolite Identification | Characteristic Product Ions (m/z) | Matrix |
|---|---|---|---|---|---|
| M20 | 36.96[a] 37.94[b] | 546 | (structure) | 466, 307, 289, 161 | Plasma |

Figure 8:
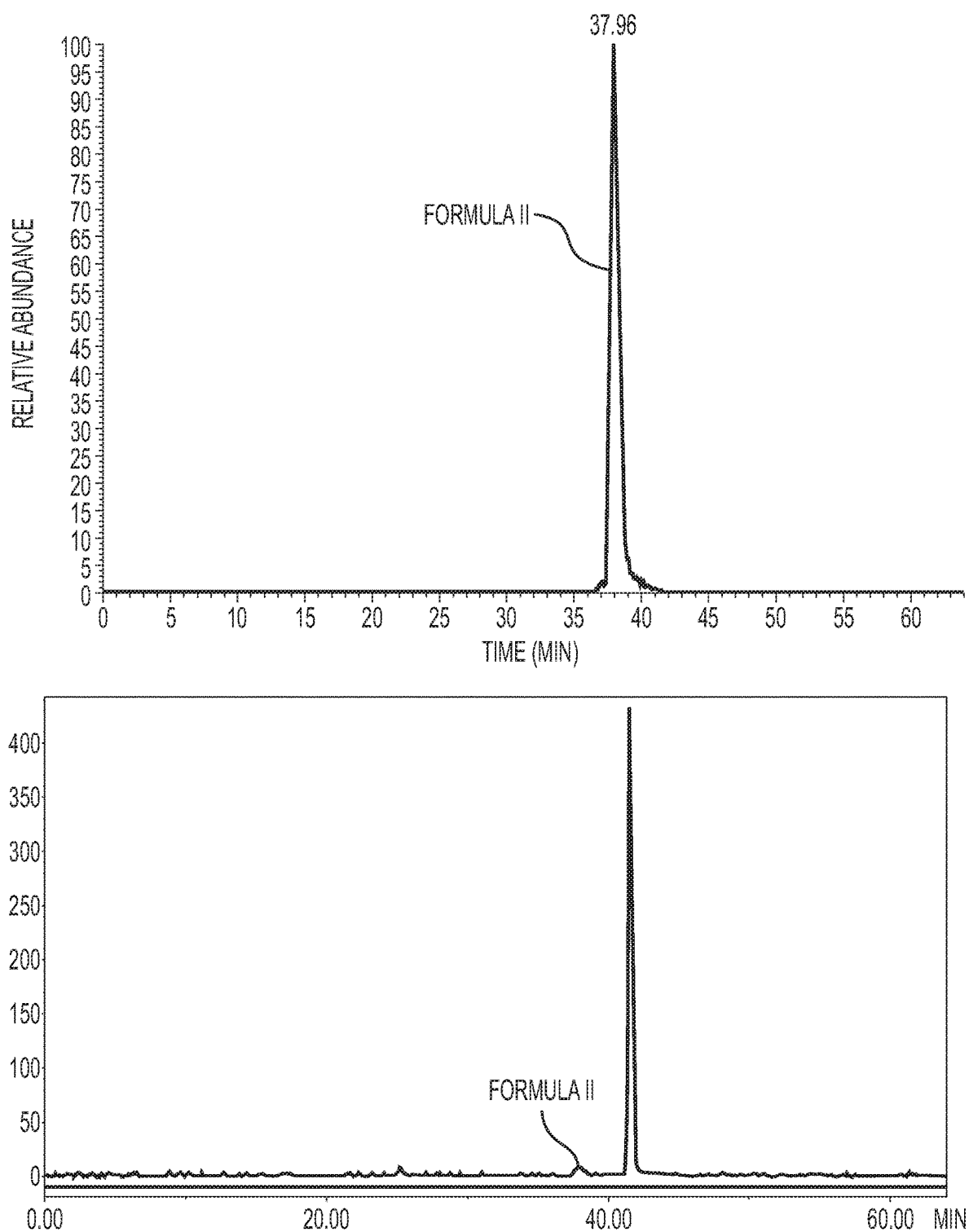
FIG. 8 shows an extracted ion chromatogram and radiochromatogram from analysis of an 8-hour pooled plasma sample obtained after administration of a single oral dose of [$^{14}$C]bictegravir to male human subjects (100 mg, 100 μCi).
Figure 9:
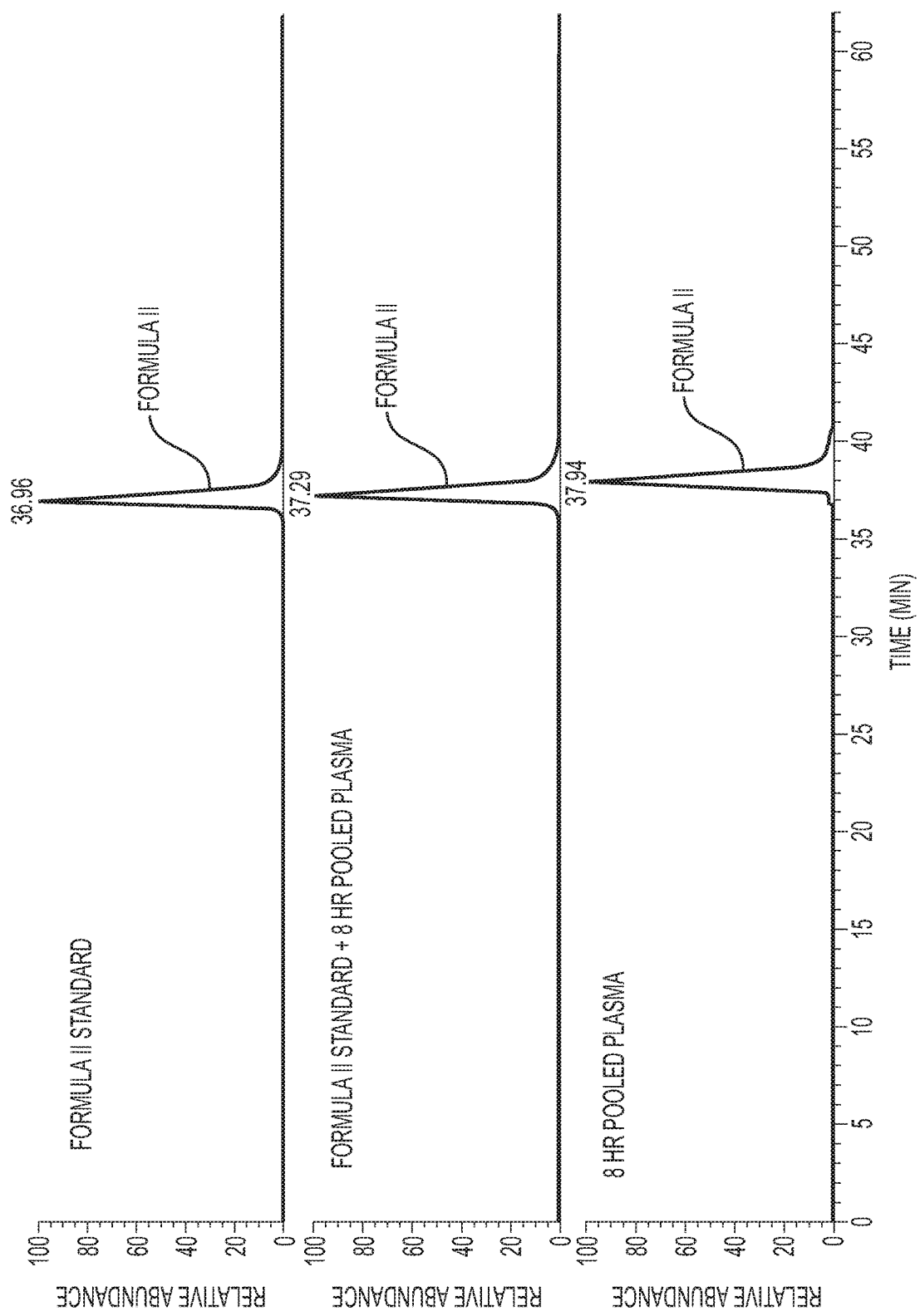
FIG. 9 shows extracted ion chromatograms from individual injections and a co-injection of a standard solution of M20 with an 8-hour pooled plasma sample obtained after administration of a single oral dose of [$^{14}$C]bictegravir to male human subjects (100 mg, 100 μCi).

[a] Retention time from analysis of a standard solution of M20 (Figure 7).
[b] Retention time from analysis of a plasma sample (Figure 8).

TABLE 6

| Metabolite Designation | Measured Mass | Theoretical Mass | Proposed Formula | Δ mDa | Δ ppm |
|---|---|---|---|---|---|
| M20 | 546.0793 | 546.0789 | $C_{21}H_{19}F_3N_3O_9S^+$ | 0.40 | 0.7 |

Δ mDa = (Measured mass − Theoretical Mass) * 1000.
Δ ppm = (Δ mDa/Theoretical Mass) * 1000.

Example 5: In Vitro Assessment of Human MRP2 Inhibition Potential of BIC, M15, M20 and M23

Assay Methodology

Inhibition of the hepatic efflux transporter multidrug-resistance protein 2 (MRP2; ABCC2) by bictegravir and its metabolites (M15, M20 and M23) was studied in the following assay. Cells and experimental conditions for the transporter inhibition assays are summarized below in Table 7. BIC can be synthesized according to the procedures described, for example, in WO 2014/100212. M15, M20, and M23 were prepared according to the procedures described herein. All other materials were purchased by SOLVO Biotechnology and experiments were conducted according to SOLVO Standard Operating Procedures (SOPs) of its certified ISO 9001:2008 system. Lot and product information was recorded by SOLVO Biotechnology.

TABLE 7

| Transporter | System | Model Substrate | Positive Control |
|---|---|---|---|
| MRP2 | Membrane Vesicles | $^3$H-$E_2$17βG | Benzbromarone |

($E_2$17βG) Estradiol-17beta-glucuronide

Inhibition of Transport in Membrane Vesicles

Test compounds and positive control was incubated with membrane vesicle preparations (total protein: 50 μg/well) and the model substrate in the absence or presence of ATP. Reaction mixtures were preincubated for 15 minutes at 37° C. Reactions were started by the addition of 25 μL of 12 mM MgATP or AMP assay buffer (for background controls) preincubated separately. Reactions were stopped after 5 min by the addition of 200 μL of ice-cold washing buffer and immediate filtration via glass fiber filters mounted to a 96-well plate (filter plate). The filters were washed, dried and the amount of substrate inside the filtered vesicles determined by liquid scintillation. A positive control inhibitor was tested in parallel. Control membranes lacking transporter expression were used as negative control. All assays were performed in duplicate.

Fractional transport activities were calculated from the following equation:

Activity %=(A−B)/(C−D)×100 where A is translocated amount of substrate in the presence of TA and ATP, B is translocated amount of substrate in the presence of TA, C is translocated amount of substrate in the presence of solvent and ATP, and D is translocated amount of substrate in the presence of solvent.

$IC_{50}$ Determination in Transporter Assays $IC_{50}$ is defined as the test article concentration needed to inhibit the maximal transporter specific transport by 50%. $IC_{50}$ values were calculated using non-linear fitting of % inhibition versus concentration to a sigmoidal curve with a variable Hill Coefficient using GraphPad Prism 5 (GraphPad Software Inc., San Diego, Calif.). If the % inhibition was less than 50% at the highest concentration tested, the $IC_{50}$ was not determined. No inhibition observed (NIO) is reported for relative inhibition results <20% and no concentration dependent transport observed up to the highest concentration tested.

Inhibition data are summarized in Table 8. The positive control benzbromarone at 200 μM showed ≥99% inhibition in each assay. BIC showed no inhibition of MRP2-mediated $E_2$17βG at concentrations up to 100 μM. M15 and M20 showed dose dependent inhibited MRP2 mediated transport of E217βG with calculated $IC_{50}$ values of 256 μM and 45 μM, respectively. Precipitation was observed at the highest investigated concentration of 300 μM in assay buffer for M20. M23 showed 43% inhibition of MRP2 mediated transport at highest test concentration of 100 μM.

TABLE 8

Uptake Transporter Inhibition Assay

| Compound | Maximum inhibition observed (% of control) | $IC_{50}$ (μM) |
|---|---|---|
| BIC | 0% at 100 μM | NIO |
| M15 | 53% at 300 μM | 256 |
| M20 | 98% at 300 μM | 45 |
| M23 | 43% at 100 μM | >100 |

Example 6: In Vitro Assessment of Human OATP Inhibition Potential of BIC, M15, M20 and M23

Assay Methodology

The inhibition of the human uptake transporter organic anion-transporting polypeptide 1B1, 1B3 and 2B1

(OATP1B1, OATP1B3, OATP2B1; SLC) by BIC and its metabolites (M15, M20 and M23) was studied in the following assay.

Cells and experimental conditions for the transporter inhibition assays are summarized below in Table 9. BIC can be synthesized according to the procedures described, for example, in WO 2014/100212. M15, M20, and M23 were prepared according to the procedures described herein.

TABLE 9

| Transporter | Test System | Model Substrate | Positive Control |
|---|---|---|---|
| OATP1B1/OATP1B3 | CHO Cells | Fluo-3 | Rifampicin |
| OATP1B1/OATP1B3 | HEK293FT Cells | $^3$H-E$_2$17βG | Rifampicin |
| OATP2B1 | MDCKII | $^3$H-E3S | Fluvastatin |

(HEK293FT) Fast growing human embryonic kidney cells transformed with the SV40 large T antigen
(E$_2$17βG) Estradiol-17beta-glucuronide
(E3S) Estrone-3-sulfate
(MDCKII) Madin Darby Canine Kidney subclone II OATP1B1 and OATP1B3 Inhibition Assay Using Fluo-3 as the Probe Substrate Chinese Hamster Ovary (CHO) cells, either wild type or transfected with the genes encoding human OATP1B1 or OATP1B3, were maintained in Dulbecco's Modification of Eagle's Medium (DMEM) containing 1,000 mg/L D-glucose, L-glutamine, 25 mM HEPES buffer, and 110 mg/L sodium pyruvate, 1% Pen/Strep, 10% fetal bovine serum, 0.05 mg/mL L-proline and 0.5 mg/mL of geneticin G-418. Cells were maintained in incubators set at 37° C., 90% humidity and 5% CO$_2$. OATP1B1 or OATP1B3 overexpressing CHO cells were seeded in BioCoat Poly-D-Lysine coated 96 well black cell culture plates with clear bottoms at a density of 1×10$^5$ cells/well. Sodium butyrate (10 mM) was added to the OATP1B1 and OATP1B3 cells to increase the protein expression level, and the cells were grown to confluence overnight. The assay buffer contained 142 mM NaCl, 5 mM KCl, 1 mM KH$_2$PO$_4$, 1.2 mM MgSO$_4$, 1.5 mM CaCl$_2$, 5 mM Glucose and 12.5 mM HEPES (pH 7.4). After removal of the media and before adding test compounds, the cells were washed twice with 37° C. assay buffer followed by a 0.5 h pre-incubation with assay buffer. Test compounds were serially diluted in DMSO at 250-fold of final test concentrations to create the compound spiking solutions. Compounds were then spiked into assay buffer containing 2 µM Fluo-3 and incubated with cells for 1 h. Following removal of assay buffer containing Fluo-3 and test compound, cells were washed 3 times with 200 µl of ice cold assay buffer and then lysed at room temperature for 15 minutes in a lysis buffer containing 0.05 SDS in a 1 mM CaCl$_2$ solution. Substrate accumulations were determined for Fluo-3 fluorescence at an excitation of 485 nm and emission of 530 nm.

OATP1B1 and OATP1B3 Inhibition Assay Using $^3$H-E$_2$17βG as the Probe Substrate HEK293FT-Mock and OATP-transfected cells (1×10$^5$ cells each) were seeded 24 hr prior to assay. Pre-rinsed ells were incubated for 3 minutes with 1 µM $^3$H-E$_2$17βG in HK buffer in the presence of various concentrations of test compound or positive control rifampicin. After the experiment cells were rinsed with Krebs-Henseleit buffer and lysed with 0.1 M NaOH. The amount of substrate inside the cells was determined by liquid scintillation reader.

OATP2B1 Inhibition Assay

MDCKII-Mock and OATP2B1-transfected cells (1×10$^5$ cells each) were seeded 24 hr prior to assay. Pre-rinsed cells were incubated for 2 minutes with 0.2 µM $^3$H-E3S in HK buffer in the presence of various concentrations of test compound or positive control fluvastatin. After the experiment cells were rinsed with Krebs-Henseleit buffer and lysed with 0.1 M NaOH. The amount of substrate inside the cells was determined by liquid scintillation reader.

Data Analysis for OATP Inhibition Assays

Percent inhibition was calculated according to the following equation:

% inhibition=[1−{[OATP]$i$−[WT]$ni$}/{[OATP]$ni$−[WT]$ni$}]*100 where:

[OATP]i represent the substrate accumulation in the presence of test compound for either OATP1B1, OATP1B3, or OATP2B1 cells;

[OATP]ni represents the substrate accumulation in the absence of test compound for either OATP1B1, OATP1B3, or OATP2B1 cells, respectively; and

[WT]ni represents the substrate accumulation in the absence of test compound for wild type cells or Mock cells, respectively.

IC$_{50}$ Determination in Transporter Assays

IC$_{50}$ was determined according to the procedures described in Example 5. The positive control inhibitors for each transporter showed >80% inhibition in each assay. The highest concentration of BIC, M15, M20 and M23 assayed was 100, 100, 300 and 100 µM, respectively. IC$_{50}$ were not determined for compounds with <20% inhibition or no dose dependent inhibition observed. Results are reported as NIO (no interaction observed).

BIC showed no inhibition of OATP1B1-mediated estradiol-17beta-glucuronide (E$_2$17βG) transport at highest test concentration of 100 µM. BIC inhibited 17% of estrone-3-sulfate uptake by OATP2B1 cells at highest test concentration 100 µM. Data for BIC is summarized in Table 10.

TABLE 10

| Transporter | Probe Substrate Used | Maximum inhibition at highest test conc. (% of control) | IC$_{50}$ (µM) |
|---|---|---|---|
| OATP1B1 | E$_2$17βG | 0% inhibition at 100 µM | NIO |
| OATP1B3 | E$_2$17βG | 6% inhibition at 100 µM | NIO |
| OATP2B1 | E3S | 17% inhibition at 100 µM | NIO |

M15 showed 39% inhibition of OATP1B1-mediated and no inhibition of OATP1B3-mediated transport of Fluo-3 transport at highest test concentration of 100 µM. Data for M15 is summarized in Table 11.

TABLE 11

| Transporter | Probe Substrate Used | Maximum inhibition at highest test conc. (% of control) | IC$_{50}$ (µM) |
|---|---|---|---|
| OATP1B1 | Fluo-3 | 39% inhibition at 100 µM | >100 |
| OATP1B3 | Fluo-3 | 0% inhibition at 100 µM | NIO |

M20 showed 12% inhibition of OATP1B1-mediated and 49% of OATP1B3-mediated transport of estradiol-17beta-glucuronide (E$_2$17βG) transport at highest test concentration of 100 µM. M20 inhibited OATP1B1-mediated Fluo-3 transport with IC$_{50}$ value of 90.1 µM and 18% of OATP1B3-mediated Fluo-3 transport at 100 µM. M20 inhibited 26% of estrone-3-sulfate uptake by OATP2B1 cells at highest test concentration 100 µM. Data for M20 is summarized in Table 12.

TABLE 12

| Transporter | Probe Substrate Used | Maximum inhibition at highest test conc. (% of control) | IC$_{50}$ (µM) |
|---|---|---|---|
| OATP1B1 | E$_2$17βG | 12% inhibition at 100 µM | NIO* |
| OATP1B3 | E$_2$17βG | 49% inhibition at 100 µM | >100* |
| OATP1B1 | Fluo-3 | 54% inhibition at 100 µM | 90.1 |
| OATP1B3 | Fluo-3 | 18% inhibition at 100 µM | NIO |
| OATP2B1 | E3S | 26% inhibition at 100 µM | >100* |

*Precipitation of test compound observed at 300 µM test concentration in assay buffer. Data at 300 µM was not used for determination of IC$_{50}$ values.

M23 inhibited OATP1B1-mediated Fluo-3 transport with IC$_{50}$ value of 99.9 µM and 20% of OATP1B3-mediated transport of Fluo-3 transport at highest test concentration of 100 µM. Data for M23 is summarized in Table 13.

TABLE 13

| Transporter | Probe Substrate Used | Maximum inhibition at highest test conc. (% of control) | IC$_{50}$ (µM) |
|---|---|---|---|
| OATP1B1 | Fluo-3 | 51% inhibition at 100 µM | 99.9 |
| OATP1B3 | Fluo-3 | 20% inhibition at 100 µM | NIO |

Overall, BIC showed no dose dependent inhibition toward OATP1B1, OATP1B3 and OATP2B1-mediated transport at concentrations up to 100 µM. M15, M20 and M23 inhibited OATP1B1-mediated Fluo-3 transport with IC$_{50}$ of >100, 90.1, and 99.9 µM, respectively. M15, M20, and M23 showed minimal to no inhibition with OATP1B3-mediated Fluo-3 transport at concentrations up to 100 µM. M20 showed no dose dependent inhibition of OATP1B1-mediated E$_2$17βG transport but inhibited both OAT1B3-mediated E$_2$17βG transport and OATP2B1-mediated estrone-3-sulfate transport with IC$_{50}$ of >100 µM. For inhibition≤20% at highest test concentration, no IC$_{50}$ value was reported.

Example 7: In Vitro Assessment of Inhibition Potential of Bictegravir and its Metabolites for Human Hepatic Microsomal Bilirubin Glucuronidation In this example, the potential for bictegravir and its metabolites, M15, M20, and M23 to reduce the catalytic activity of human hepatic microsomal UGT1A1 was determined, as assayed by bilirubin glucuronidation. In this assay, The rates of enzyme-specific metabolite formation from bilirubin substrate were quantified in the presence and absence of bictegravir and its metabolites and their IC50 values were determined. This study is useful for assessing whether there is potential for bictegravir and/or its metabolites to undergo pharmacokinetic interactions with other drugs and with endogenous compounds. In this assay, the inhibitory effects of bictegravir and its metabolites on the activity of a major human glucuronidation enzyme, uridine diphosphate glucuronosyltransferase 1A1 (UGT1A1), responsible for conjugation of bilirubin, was assessed in vitro with the intent of determining an IC50 value.

Materials

BIC can be synthesized according to the procedures described, for example, in WO 2014/100212. M15, M20, and M23 were prepared according to the procedures described herein. Other reagents used in the assays were purchased from Sigma-Aldrich (St. Louis, Mo.) or BD Biosciences (Woburn, Mass.), except for atazanavir (Toronto Research Chemicals, North York ON). Human hepatic microsomal fraction was provided by BD Biosciences (Woburn, Mass.). Bilirubin substrate was prepared fresh immediately before starting the assay.

Enzyme Inhibition Assays

Bilirubin is metabolized by UGT1A1 yielding the two acyl monoglucuronides and the acyl diglucuronide. There is no clear preference for which of the target propionates (C8 or C12) is metabolized first. Atazanavir has been demonstrated to be a potent, selective inhibitor of this activity and is thus an appropriate positive control. The conditions for the assay were determined to be linear with respect to microsomal protein concentration and incubation time. Under the assay conditions the K$_M$ for bilirubin monoglucuronide formation was determined to be 0.98 µM and the substrate concentration of 0.8 µM used here is ≤K$_M$. Microsomal UGT1A1 activity was determined in duplicate. The final reaction mixture was composed of 0.2 mg/mL hepatic microsomal protein, 100 µg alamethicin/mg microsomal protein, 5 mM UDP-glucuronic acid, 5 mM magnesium chloride, 5 mM D-saccharic acid 1,4-lactone (SACLAC), 0.8 µM bilirubin and 0.1 M potassium phosphate buffer pH 7.4. Diluted microsomal fraction was incubated on ice for 15 minutes with alamethicin, magnesium chloride and SACLAC. Substrate and inhibitor were then added and the mixture warmed to 37° C. for 0.5 minute. The reaction was initiated by the addition of UDP glucuronic acid in potassium phosphate buffer. The incubation continued at 37° C. with shaking and no light exposure for 2 minutes. Reactions were terminated by addition of one volume of 200 mM ascorbic acid in methanol, containing 200 nM 2-(N-(2-ethylphenyl)methylsulfonamido)-N-(2-(pyridin-2-ylthio)ethyl)acetamide as the internal standard. The samples were centrifuged at 3600 rpm for 5 minutes at 4° C., and aliquots of the supernatant subject to LC-MS/MS to monitor monoglucuronide formation from bilirubin.

Liquid Chromatography—Mass Spectrometry (LC-MS)

A Shimadzu UFLC XR UPLC system was used for analysis. The column used was a Thermo-Hypersil Gold 1.9 µm C18 column (30×2.1 mm) held at 60° C. Mobile phases were; A: water containing 0.1% (v/v) formic acid, and B: acetonitrile containing 0.1% (v/v) formic acid, pumped at 0.7 mL/minute. Elution was achieved by a series of linear gradients over 2 minutes. The mass spectrometer was an Applied Biosciences SCIEX QTRAP 5500 triple quadrupole mass spectrometer with an electrospray interface operating in positive ion mode. Quantification was by metabolite/internal standard peak area ratio (PAR). Extracted samples stored in the autosampler exhibited instability of the bilirubin glucuronide signal. Loss was ~0.1%/min.

Data Analysis

LC-MS/MS Analysis

Bilirubin glucuronide standards are not available commercially so the bilirubin monoglucuronide and diglucuronide peaks were identified by their MS properties. MS/MS transitions ([M+H]+) of m/z 761.2/475.1 and 937.2/475.1 for the monoglucuronide and diglucuronide, respectively. The PAR values for the two monoglucuronides were combined for quantification. The PAR values in the presence of inhibitors were compared to those of vehicle controls (no bictegravir, M15, M20, M23, or positive control inhibitor) and activities expressed as the percentage of control activity remaining.

IC$_{50}$ Determinations

Reaction velocities were calculated from the rates of formation of the metabolites and were compared to those seen with the vehicle control (100% activity). $IC_{50}$ values were calculated by non-linear regression using GraphPad Prism 7.03 and a sigmoidal three parameter inhibition model. Weak inhibition by the test compounds necessitated constraining the lower plateau value of the model (residual activity when UGT1A1 is fully inhibited) to generate meaningful $IC_{50}$ values. During the testing period the inhibitory potency of atazanavir was determined four times, with each concentration tested in duplicate in each determination. The data from all runs were pooled and a global fit performed to determine the lower plateau value. The Best-fit value was 10.96% (standard error 2.94%) activity remaining. $IC_{50}$ values of bictegravir and its metabolites were calculated by non-linear regression with the lower plateau constrained to this value. For atazanavir, the $IC_{50}$ values from the four duplicate runs were combined to generate a summary geometric mean and multiplicative standard deviation for this positive control inhibitor.

Results

Inhibitory effects of bictegravir, M15, M20, and M23 on the activity of human hepatic microsomal bilirubin monoglucuronidation were assessed. A summary of the inhibitory potencies and for the positive control inhibitor, atazanavir, is presented in Table 14. The positive control inhibitor, atazanavir, reduced UGT1A1 activity as expected, confirming satisfactory incubation conditions for the assays (Table 1). The geometric mean $IC_{50}$ value for atazanavir obtained over the four runs was 1.2 µM. Concentrations of bictegravir and its glucuronide metabolite (M15) up to 300 µM had little or At concentrations up to 300 µM there was little or no inhibitory effect of bictegravir or M15 on human hepatic microsomal bilirubin glucuronidation (an activity catalyzed by UGT1A1). M20 and M23 were weak inhibitors with calculated $IC_{50}$ values of 153 µM and 256 µM respectively.

Figure 12:
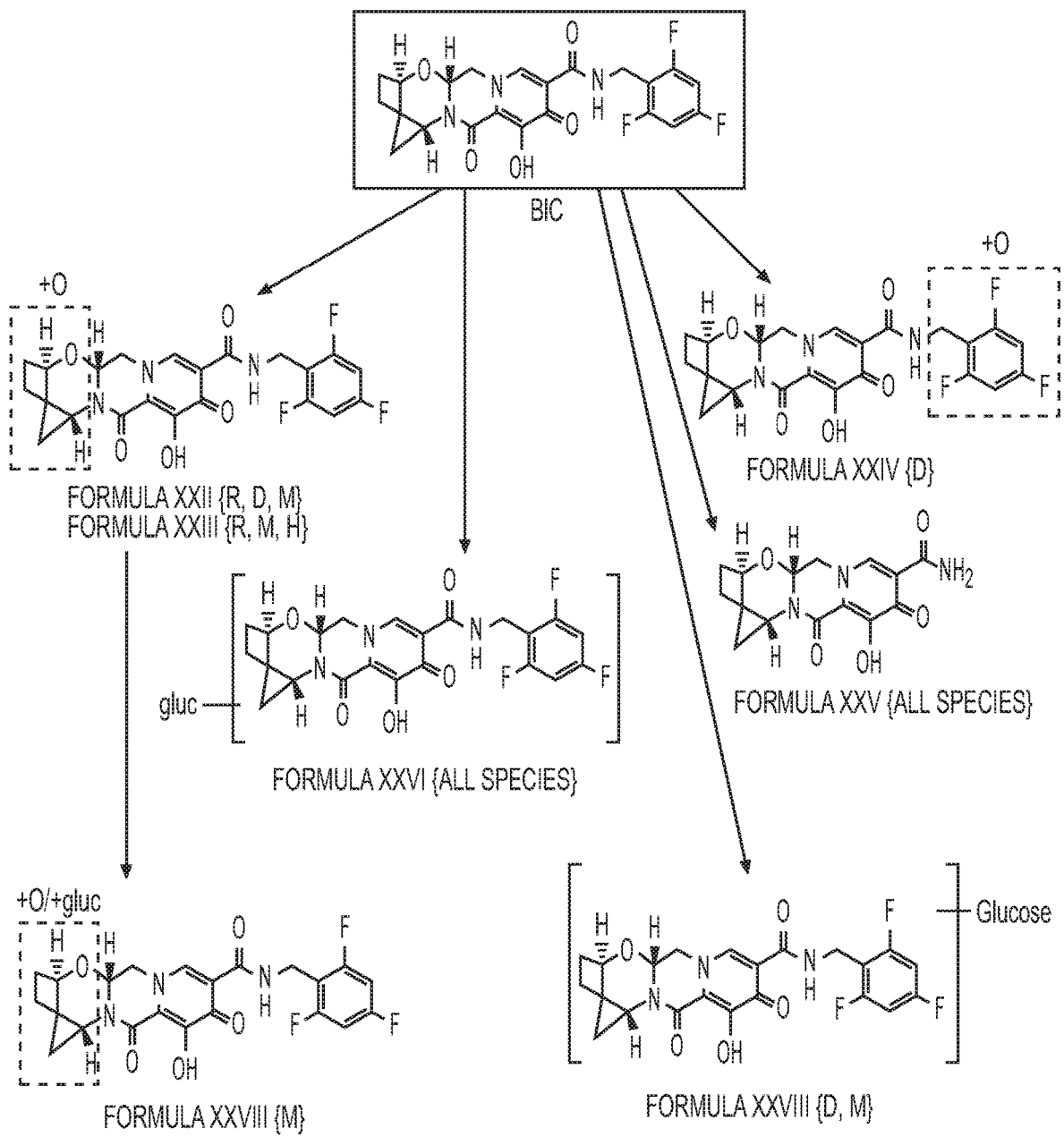
FIG. 12 shows proposed structures of BIC metabolites M465a, M465b, M465c, M305, M625, M641, and M611 identified in vitro.

Example 8: Metabolites of BIC Detected in Cyropreserved Hepatocytes from Different Species Cryopreserved hepatocytes were incubated for 4 hours with radiolabeled BIC to identify metabolites, determine their abundance and compare nonclinical species with human. The percentage of parent drug and identified metabolites following incubation with [$^{14}$C]BIC (20 µM) in cryopreserved hepatocytes are summarized in Table 15 and their proposed identities are shown in FIG. 12. Metabolic pathways included hydroxylation (3 variants), N-dealkylation, and direct glucuronidation. All human metabolites were also observed in nonclinical species. Using the hepatocyte system where the full range of hepatic metabolic enzymes are represented, it appeared that the metabolism of BIC was extensive in monkey and dog but lower in rat and human.

TABLE 15

| | | Fraction of Radiochromatogram (%) | | | |
|---|---|---|---|---|---|
| Analyte[a] | Identity | Wister-Han Rat | Beagle Dog | Cynomolgus Monkey | Human |
| BIC | Parent | 91.5 | 78.7 | 52.4 | 93.9 |
| M305 | N-dealkylation | 1.7 | 8.7 | 2.4 | 1.2 |
| M465a | Hydroxylation-1 | 1.2 | 1.4 | 2.7 | — |
| M465b | Hydroxylation-2 | — | 0.2 | 11.6 | 0.6 |
| M465c | Hydroxylation-3 | — | 3.6 | — | — |
| M611 | Glucose conjugation | — | 0.8 | 4.4 | — |
| M625 | Glucuronide conjugation | 5.2 | 6.6 | 21.7 | 4.3 |
| M641 | Hydroxylation/glucuronidation | — | — | 4.1 | — |
| Total | — | 99.6 | 100 | 99.3 | 100 |

[a]Analyte metabolite identification numbers correspond to their molecular weight, e.g., M305 = metabolite with 305 Da molecular weight.

no inhibitory effect upon UGT1A1 activity (inhibition<2%). There was modest stimulation of enzyme activity at high concentrations of these two test compounds, reaching peak increases of 76% at 200 µM bictegravir and 21% at 200 µM M15Bictegravir metabolites M20 and M23 were weak inhibitors of human hepatic bilirubin glucuronidation with $IC_{50}$ values of 153 and 256 µM, respectively.

TABLE 14

| | Calculated $IC_{50}$ (µM) | | | | |
|---|---|---|---|---|---|
| Activity | Atazanavir (Control) | Bictegravir | M15 | M20 | M23 |
| Bilirubin monoglucuronidation | 1.2 (1.44)[a] | >300[b] (NIO) | >300[b] (NIO) | 153[c] | 256[c] |

NIO No inhibition observed (<2% inhibition over the concentration range 0-300 µM)
[a]Geometric mean and multiplicative standard deviation for four determinations in duplicate runs.
[b]Fit did not converge. Maximum concentration tested was 300 µM.
[c]Best-fit value using 8 duplicate datapoints Example 9. In Vivo BIC Metabolism in Different Species Bictegravir metabolism was determined following a single oral administration of [$^{14}$C]BIC to mouse, rat, monkey, and human. Pooled plasma, urine, bile, and fecal samples obtained following in vivo oral administration of [$^{14}$C]BIC were profiled and a comprehensive listing of the identified metabolites are provided in transgenic mice, Wistar-Han rats, monkeys, and healthy human subjects. The combined results demonstrate that BIC is mainly eliminated by hepatic metabolism followed by excretion into feces and urine. Metabolic pathways included hydroxylation, oxidative defluorination, direct glucuronidation, and oxidation followed by phase II conjugation. In the monkey, BIC was metabolized through the oxidative pathways to a greater extent compared to rat and human. Results of the plasma profile following oral administration of [$^{14}$C]BIC is shown below in Table 16.

TABLE 16

| | % of Total Radioactivity in AUC Pooled Plasma[a] | | | |
|---|---|---|---|---|
| Component | Transgenic Mouse | Wistar Han Rat | Cynomolgus Monkey | Human |
| BIC | 95.5 | 76.5 | 80.2 | 67.9 |
| M12 | 1.86 | 2.18 | ND | ND |
| M15 | ND | ND | 0.55 | 8.6 |
| M20 | ND | 11.3 | 0.77 | 20.1 |
| M21/M22 | ND | 1.18 | ND | 2.0 |
| M23 | ND | 2.36 | ND | 0.2[c] |
| M42 | ND | ND | 12.2 | ND |
| Other[b] | 0.64 | 2.36 | 3.44 | 0.6 |
| Total | 98.0 | 95.9 | 97.2 | 99.4 |

ND = not detected
[a]AUC pool plasma = area under the plasma $^{14}$C concentration-time curve from time zero to 48 hours post dose in transgenic mice, from time zero to 168 hours post dose in rats, from time zero to 72 hours post dose in monkeys, and from time zero to 72 hours post dose in human subjects.
[b]Other = sum of other metabolites; each component <1% in mouse; <1.5% in rat, monkey, and human.
[c]Co-eluted with M51.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A preparation of a compound selected from M15, M20, and M23:

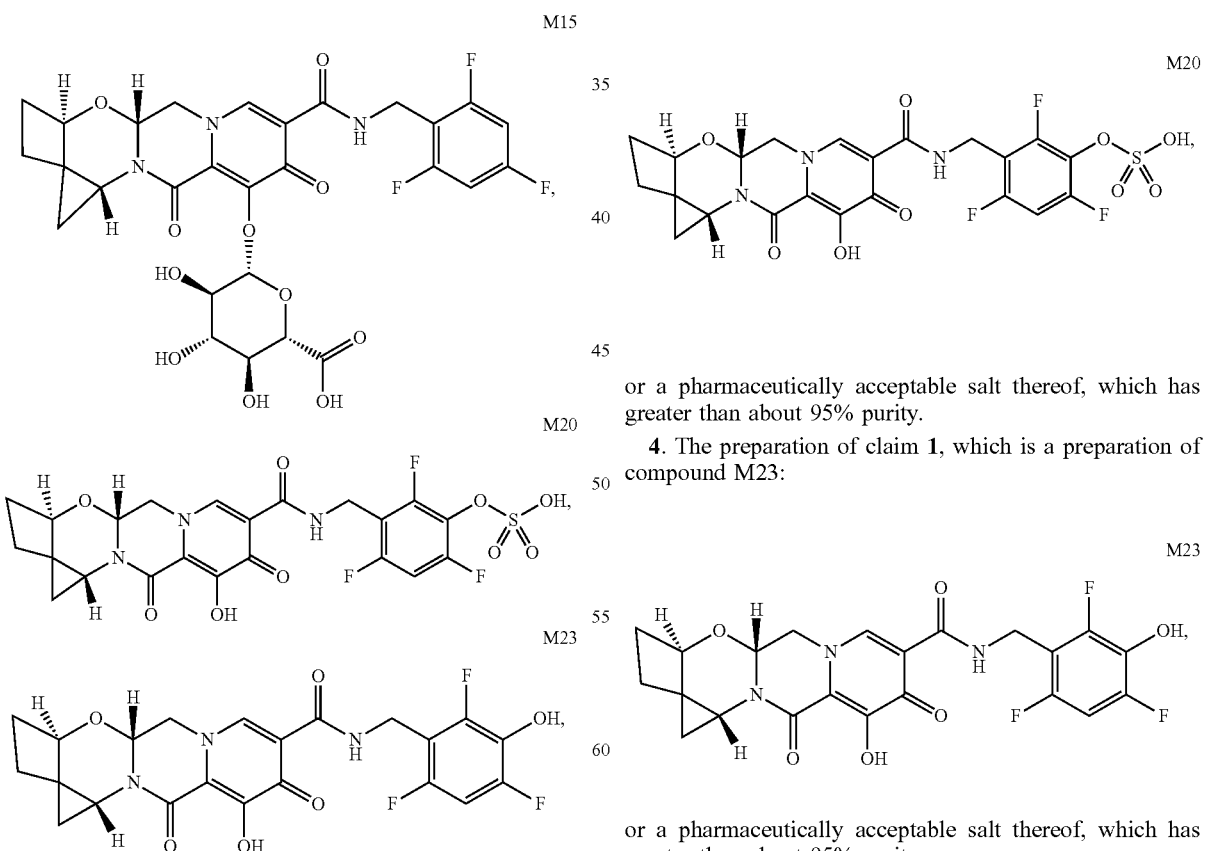

or a pharmaceutically acceptable salt thereof, which has greater than about 95% purity.

2. The preparation of claim 1, which is a preparation of compound M15:

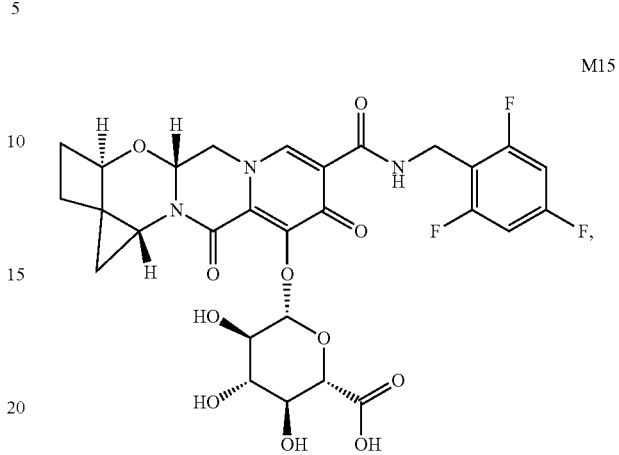

or a pharmaceutically acceptable salt thereof, which has greater than about 95% purity.

3. The preparation of claim 1, which is a preparation of compound M20:

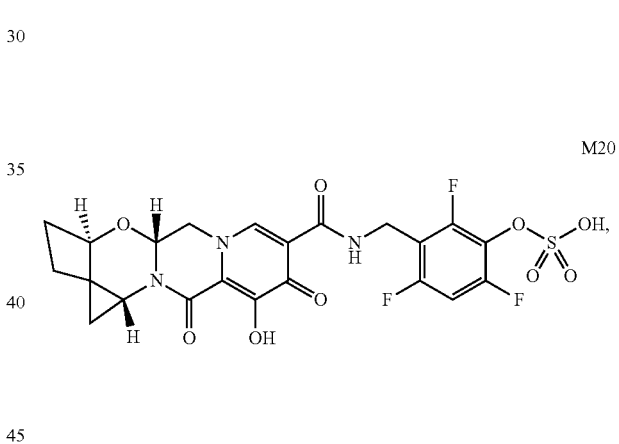

or a pharmaceutically acceptable salt thereof, which has greater than about 95% purity.

4. The preparation of claim 1, which is a preparation of compound M23:

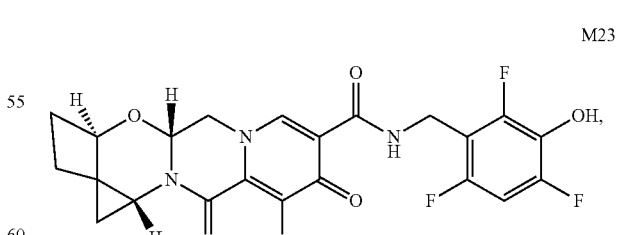

or a pharmaceutically acceptable salt thereof, which has greater than about 95% purity.

* * * * *